(12) United States Patent
Monwar et al.

(10) Patent No.: US 11,780,786 B2
(45) Date of Patent: Oct. 10, 2023

(54) TRANSITION METAL-CATALYZED PRODUCTION OF ALCOHOL AND CARBONYL COMPOUNDS FROM HYDROCARBONS

(71) Applicant: Chevron Phillips Chemical Company LP, The Woodlands, TX (US)

(72) Inventors: Masud M. Monwar, Bartlesville, OK (US); Jared L. Barr, Bartlesville, OK (US); Carlos A. Cruz, Kingwood, TX (US); Kathy S. Clear, Bartlesville, OK (US); Max P. McDaniel, Bartlesville, OK (US); William Chad Ellis, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 153 days.

(21) Appl. No.: 17/470,066

(22) Filed: Sep. 9, 2021

(65) Prior Publication Data

US 2022/0081370 A1    Mar. 17, 2022

Related U.S. Application Data

(60) Provisional application No. 63/077,761, filed on Sep. 14, 2020.

(51) Int. Cl.
| | | |
|---|---|---|
| *C07B 33/00* | (2006.01) | |
| *C07C 29/48* | (2006.01) | |
| *C07C 45/27* | (2006.01) | |
| *C07C 51/16* | (2006.01) | |
| *C07C 29/50* | (2006.01) | |
| *C07C 45/28* | (2006.01) | |
| *C07C 51/225* | (2006.01) | |
| *B01J 21/06* | (2006.01) | |
| *B01J 21/08* | (2006.01) | |
| *B01J 21/12* | (2006.01) | |
| *B01J 23/22* | (2006.01) | |
| *B01J 23/28* | (2006.01) | |
| *B01J 23/30* | (2006.01) | |
| *B01J 35/10* | (2006.01) | |
| *B01J 37/08* | (2006.01) | |
| *B01J 37/34* | (2006.01) | |
| *B01J 38/02* | (2006.01) | |
| *B01J 35/00* | (2006.01) | |
| *B01J 37/16* | (2006.01) | |

(52) U.S. Cl.
CPC ............. *C07B 33/00* (2013.01); *B01J 21/063* (2013.01); *B01J 21/08* (2013.01); *B01J 21/12* (2013.01); *B01J 23/22* (2013.01); *B01J 23/28* (2013.01); *B01J 23/30* (2013.01); *B01J 35/004* (2013.01); *B01J 35/1014* (2013.01); *B01J 35/1019* (2013.01); *B01J 35/1023* (2013.01); *B01J 35/1028* (2013.01); *B01J 35/1038* (2013.01); *B01J 35/1042* (2013.01); *B01J 35/1047* (2013.01); *B01J 37/082* (2013.01); *B01J 37/16* (2013.01); *B01J 37/34* (2013.01); *B01J 37/345* (2013.01); *B01J 38/02* (2013.01); *C07C 29/48* (2013.01); *C07C 29/50* (2013.01); *C07C 45/27* (2013.01); *C07C 45/28* (2013.01); *C07C 51/16* (2013.01); *C07C 51/225* (2013.01)

(58) Field of Classification Search
None
See application file for complete search history.

(56) References Cited

U.S. PATENT DOCUMENTS

| | | |
|---|---|---|
| 2,857,442 A | 10/1958 | Hay |
| 3,166,537 A | 1/1965 | Gregg |
| 3,201,476 A | 8/1965 | Baker |
| 3,242,099 A | 3/1966 | Manyik |
| 3,245,179 A | 4/1966 | Hawkins |
| 3,694,422 A | 9/1972 | Long |
| 3,857,901 A | 12/1974 | Dowden |
| 3,887,494 A | 6/1975 | Dietz |
| 4,248,735 A | 2/1981 | McDaniel |
| 4,393,253 A | 7/1983 | Michaelson |
| 4,460,756 A | 7/1984 | McDaniel |
| 4,501,885 A | 2/1985 | Sherk |
| 4,588,790 A | 5/1986 | Jenkins, III |
| 4,794,096 A | 12/1988 | Ewen |
| 4,808,561 A | 2/1989 | Welborn, Jr. |
| 5,220,080 A | 6/1993 | Lyons |
| 5,352,749 A | 10/1994 | Dechellis |
| 5,436,304 A | 7/1995 | Griffin |
| 5,565,175 A | 10/1996 | Hottovy |
| 5,575,979 A | 11/1996 | Hanson |
| 5,576,259 A | 11/1996 | Hasegawa |
| 5,635,438 A | 6/1997 | Cowfer |
| 5,641,842 A | 6/1997 | McDaniel |
| 5,739,220 A | 4/1998 | Shamshoum |
| 5,807,938 A | 9/1998 | Kaneko |
| 5,919,983 A | 7/1999 | Rosen |
| 5,955,557 A | 9/1999 | Machida |

(Continued)

FOREIGN PATENT DOCUMENTS

| | | |
|---|---|---|
| CN | 1150766 C | 5/2004 |
| CN | 101264953 B | 8/2010 |

(Continued)

OTHER PUBLICATIONS

International Search Report and Written Opinion, PCT/US2021/049690, dated May 1, 2022, 12 pages.

(Continued)

*Primary Examiner* — Amy C Bonaparte
(74) *Attorney, Agent, or Firm* — Merchant & Gould P.C.

(57) ABSTRACT

Processes for converting a hydrocarbon reactant into an alcohol compound and/or a carbonyl compound are disclosed in which the hydrocarbon reactant and a supported transition metal catalyst—containing molybdenum, tungsten, or vanadium—are irradiated with a light beam at a wavelength in the UV-visible spectrum, optionally in an oxidizing atmosphere, to form a reduced transition metal catalyst, followed by hydrolyzing the reduced transition metal catalyst to form a reaction product containing the alcohol compound and/or the carbonyl compound.

17 Claims, No Drawings

(56) References Cited

U.S. PATENT DOCUMENTS

| | | |
|---|---|---|
| 6,239,235 B1 | 5/2001 | Hottovy |
| 6,262,191 B1 | 7/2001 | Hottovy |
| 6,310,167 B1 | 10/2001 | Kanzawa |
| 6,380,444 B1 | 4/2002 | Bjerrum |
| 6,518,375 B1 | 2/2003 | Monoi |
| 6,825,377 B1 | 11/2004 | Beller |
| 6,833,415 B2 | 12/2004 | Kendrick |
| 7,112,643 B2 | 9/2006 | McDaniel |
| 7,238,756 B2 | 7/2007 | Ehrman |
| 7,294,599 B2 | 11/2007 | Jensen |
| 7,304,199 B2 | 12/2007 | Xu |
| 7,326,760 B2 | 2/2008 | Cann |
| 7,407,591 B2 | 8/2008 | De Battisti |
| 7,531,606 B2 | 5/2009 | Hendrickson |
| 7,598,327 B2 | 10/2009 | Shaw |
| 7,601,665 B2 | 10/2009 | McDaniel |
| 7,648,940 B2 | 1/2010 | Holtcamp |
| 7,649,062 B2 | 1/2010 | Matsunaga |
| 7,884,163 B2 | 2/2011 | McDaniel |
| 7,956,138 B2 | 6/2011 | Holtcamp |
| 8,114,353 B2 | 2/2012 | Benham |
| 8,114,946 B2 | 2/2012 | Yang |
| 8,309,485 B2 | 11/2012 | Yang |
| 8,623,973 B1 | 1/2014 | McDaniel |
| 8,703,886 B1 | 4/2014 | Yang |
| 8,822,608 B1 | 9/2014 | Bhandarkar |
| 8,969,228 B2 | 3/2015 | Nazarpoor |
| 9,006,367 B2 | 4/2015 | McDaniel |
| 9,023,959 B2 | 5/2015 | McDaniel |
| 9,096,699 B2 | 8/2015 | McDaniel |
| 9,169,337 B2 | 10/2015 | Rohatgi |
| 9,273,170 B2 | 3/2016 | Hlavinka |
| 9,346,897 B2 | 5/2016 | Cui |
| 9,394,393 B2 | 7/2016 | Hlavinka |
| 9,758,599 B2 * | 9/2017 | Ding .................... C08F 210/16 |
| 9,796,798 B2 | 10/2017 | Praetorius |
| 9,802,841 B2 | 10/2017 | Maruo |
| 9,815,925 B2 | 11/2017 | Lam |
| 9,988,468 B2 | 6/2018 | McDaniel |
| 10,000,594 B2 | 6/2018 | Hlavinka |
| 10,213,766 B2 | 2/2019 | Praetorius |
| 10,246,528 B2 | 4/2019 | McDaniel |
| 10,287,369 B2 | 5/2019 | Schwerdtfeger |
| 10,358,506 B2 | 7/2019 | Ding |
| 10,435,527 B2 | 10/2019 | Praetorius |
| 10,442,881 B2 | 10/2019 | Hlavinka |
| 10,654,953 B2 | 5/2020 | McDaniel |
| 10,835,890 B2 | 11/2020 | Cann |
| 10,858,459 B2 | 12/2020 | McDaniel |
| 11,180,435 B2 | 11/2021 | Cruz |
| 2004/0059070 A1 | 3/2004 | Whitte |
| 2007/0219085 A1 | 9/2007 | De Battisti |
| 2008/0032886 A1 | 2/2008 | Yeh |
| 2013/0206453 A1 | 8/2013 | Fagrell |
| 2014/0221692 A1 | 8/2014 | Netemeyer |
| 2015/0191554 A1 | 7/2015 | McDaniel |
| 2017/0073439 A1 | 3/2017 | Ewart |
| 2017/0274356 A1 | 9/2017 | Cann |
| 2018/0079845 A1 | 3/2018 | Doufas |
| 2019/0153129 A1 | 5/2019 | McDaniel |
| 2019/0184389 A1 | 6/2019 | Neygandhi |
| 2019/0308172 A1 | 10/2019 | Zou |
| 2020/0086307 A1 | 3/2020 | Monwar |
| 2020/0087430 A1 | 3/2020 | Clear |
| 2020/0239605 A1 | 7/2020 | McDaniel |
| 2021/0077981 A1 | 3/2021 | Cruz |
| 2021/0078920 A1 | 3/2021 | Cruz |
| 2021/0078926 A1 | 3/2021 | Barr |
| 2021/0078927 A1 | 3/2021 | McDaniel |
| 2022/0081370 A1 | 3/2022 | Monwar |

FOREIGN PATENT DOCUMENTS

| | | |
|---|---|---|
| CN | 108203476 A | 6/2018 |
| CN | 106317267 B | 12/2018 |
| CN | 104774280 B | 9/2019 |
| CN | 106893015 B | 9/2019 |
| CN | 108439533 B | 7/2020 |
| CN | 107311263 B | 11/2020 |
| CN | 107108800 B | 3/2021 |
| JP | H05310601 A | 11/1993 |
| JP | 2010132597 A | 6/2010 |
| JP | 2012101986 A | 5/2012 |
| WO | 2020060888 A2 | 3/2020 |
| WO | 2020060889 A2 | 3/2020 |
| WO | 2021055270 A1 | 3/2021 |
| WO | 2021055271 A1 | 3/2021 |
| WO | 2021055272 A1 | 3/2021 |

OTHER PUBLICATIONS

Economy, et.al., "Supported Barium Chromate—A New Oxidation Catalyst", J. Catalysis, vol. 4, No. 4, Aug. 1, 1965, pp. 146-153.

Kentaro et. al., "Selective photo-oxidation of neat cyclohexane in the liquid phase over V2O5/Al2O3", Journal of Molecular Catalysis A: Chemical, vol. 208, No. 1-2, (Feb. 1, 2004), pp. 299-305.

McDaniel, et. al., "The Activation Of The Phillips Polymerization Catalyst; I. Influence Of The Hydroxyl Population", J. Catalysis, vol. 82, No. 1, Jul. 1, 1983, pp. 98-109.

Takenaka S et. al., "Effect of alkali-metal ion addition to silica-supported molybdenum oxide on photocatalysis", Journal of The Chemical Society, Faraday Transactions, vol. 94, No. 5, (Mar. 7, 1998), pp. 695-700. DOI: 10.1039/A707471I.

Tanaka et. al., "Enhanced photocatalytic activity of quantum-confined tungsten trioxide nanoparticles in mesoporous silica", Chemical Communications, vol. 46, No. 29, (Jan. 1, 2010), p. 5286. DOI: 10.1039/c0cc00540a.

Search Report issued in related Chinese Application No. 2019800569668, dated Nov. 3, 2022, 4 pp.

Awasthy, A.K. and Jan Rocek, "The Nature of the Transition State in the Oxidation of Olefins by Chromium (VI)," JACS 91;4, Feb. 12, 1969, pp. 991-996.

Baker, et. al., Oxidation of olefins by supported chromium oxide, The Journal of Organic Chemistry, vol. 33, No. 2, pp. 616-618 (Year: 1968).

Milas, N .A., The hydroxylation of unsaturated substances. III. The use of vanadium pentoxide and chromium trioxide as Catalysts of hydroxylation, The Journal of the American Chemical Society, vol. 59, No. 11, pp. 2342-2344 (Year: 1937).

Milas, N.A. et al., The hydroxylation of unsaturated substances. IV. The catalytic hydroxylation of unsaturated hydrocarbons, The Journal of the American Chemical Society, vol. 59, No. 11, pp. 2345-2347 (Year: 1937).

Monwar, et.al., "Ethylene polymerization by hydrocarbon-reduced Cr/silica catalyst", Journal of Catalysis 394 (2021) 451-464. DOI 10.1016/j.jcat.2020.10.019.

Barzan, et al., Ligands Make the Difference: Molecular Insights into CrVI/SiO2 Phillips Catalyst during Ethylene Polymerization, J. Am. Chem. Soc., 2017, 139, 47, 17064-17073.

Brown, et al., "Mechanism of Initiation in the Phillips Ethylene Polymerization Catalyst: Redox Processes Leading to the Active Site", ACS Catal. 2015, 5, 5574-5583.

Cainelli, et al., "Reactivity and Structure Concepts in Organic Chemistry", vol. 19, "Chromium Oxidations in Organic Chemistry", Springer Verlag Berlin 1984, p. 8.

Chakrabarti, et al., "Operando Molecular Spectroscopy During Ethylene Polymerization by Supported CrOx/SiO2 Catalysts: Active Sites,Reaction Intermediates, and Structure-Activity Relationship", Top. Catal. 2016, 59 p. 725-739.

Cruz, et al., "Identification of the Starting Group on the Initial PE Chain Produced by Phillips Catalyst", Macromolecules 2019, 52, 5750-5760.

Fendrick, Et. Al, "Actinacyclobutanes. Implementation of Thermochemically Based Strategies for the Ring-Opening Stoichiometric C—H Functionalization of Saturated and Olefinic Hydrocarbons", J. Am. Chem. Soc. 1986,108, 425-437.

Finch, "Reduction Studies on Supported Chromic Anhydride Catalysts," Journal of Catalysis, 43, 1976, pp. 111-121.

(56) References Cited

OTHER PUBLICATIONS

Floryan, et al., Strain Effect and Dual Initiation Pathway in Cr(III)/SiO2 Polymerization Catalysts from Amorphous Periodic Models, J. Catalysis 2017, 346, 50-56.

Gierada, et. al., "Active sites formation and their transformations during ethylene polymerization by the Phillips CrOx/SiO2 catalyst", J. Catal., 2017, 352, 314 328.

Groppo, et al., "The Structure of Active Centers and the Ethylene Polymerization Mechanism on the Cr/SiO2 Catalyst: A Frontier for the Characterization Method", Chem. Rev. 2005, 105, 115-183.

Joseph, et al., "Products of the Initial Reduction of the Phillips Catalyst by Olefins", Journal of Catalysis 377 (2019) 550-564.

Kissin, et al., "Chemistry of Olefin Polymerization Reactions with Chromium-Based Catalysts", Journal of Polymer Science: Part A: Polymer Chemistry, 2008, 46, 5330-5347.

Kohler, et al., "Infrared Spectroscopic Characterization of Chromium Carbonyl Species Formed by Ultraviolet Photoreduction of Silica-Supported Chromium(VI) in Carbon Monoxide," J. Phys. Chem. 1994, 98, pp. 4336-4342.

Mino, et al., "Photoinduced Ethylene Polymerization on the CrVI/SiO2 Phillips Catalyst," J. Phys. Chem. C 2019, 123, 13 pp. 8145-8152.

Monwar et al., Ethylene polymerization by hydrocarbon-reduced Cr/silica catalyst, Journal of Catalysis, In Press, https://doi.org/10.1016/j.jcat.2020.10.019, 2020.

Potter, et al., "Reduction of the Phillips Catalyst by Various Olefins: Stoichiometry, Thermochemistry, Reaction Products and Polymerization Activity", J. Catal. 344 (2016) 657-668.

Schwerdtfeger, E., et al., Reduction of Cr(VI) polymerization catalysts by non-olefinic hydrocarbons, Applied Catalysis A: General, 423-424, pp. 91-99 (Year: 2012).

Scott, et al. "Surface Organometallic Investigation of the Mechanism of Ethylene Polymerization by Silica-Supported Cr Catalysts", J. Chem. Eng. Sci. 2001, 56, 4155-4163.

Thompson, et al. "'Sigma-Bond metathesis' for carbon-hydrogen bonds of hydrocarbons and Sc-R (R=H, alkyl, aryl) bonds of permethylscandocene derivatives. Evidence for noninvolvement of the pi system in electrophilic activation of aromatic and vinylic C—H bonds", J. Am. Chem. Soc. 1987, 109, 203-219.

Vidal, "Metathesis of Alkanes Catalyzed by Silica-Supported Transition Metal Hydrides", Science, v 276, issue 5309, Apr. 4, 1997, pp. 99-102. DOI: 10.1126/science.276.5309.99.

Weckhuysen et al., "Alkane dehydrogenation over supported chromium oxide catalysts," Catalysis Today 51 (1999) pp. 223-232.

Zhu, et al., "Synthesis and Structural Characterization of M(PMe3)3(O2CR)2(OH2)H2 (M) Mo, W): Aqua-Hydride Complexes of Molybdenum and Tungsten", Inorg. Chem. 2005, 44, 9637-9639.

\* cited by examiner

TRANSITION METAL-CATALYZED PRODUCTION OF ALCOHOL AND CARBONYL COMPOUNDS FROM HYDROCARBONS

REFERENCE TO RELATED APPLICATION

This application claims the benefit of U.S. Provisional Patent Application No. 63/077,761, filed on Sep. 14, 2020, the disclosure of which is incorporated herein by reference in its entirety.

FIELD OF THE INVENTION

The present disclosure generally relates to methods for converting hydrocarbons into alcohols and/or carbonyls, and more particularly, relates to performing such methods with a supported molybdenum, tungsten, or vanadium catalyst.

BACKGROUND OF THE INVENTION

Alcohol compounds can be prepared by various synthesis techniques from alkanes, but such techniques often require halogens or harsh reaction conditions. Alternative reaction schemes are therefore desirable. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Aspects of this invention are directed to processes for converting a hydrocarbon reactant into an alcohol compound and/or a carbonyl compound. In an aspect, a first process can comprise (i) irradiating the hydrocarbon reactant and a supported transition metal catalyst comprising molybdenum, tungsten, vanadium, or a combination thereof, with a light beam at a wavelength in the UV-visible spectrum to reduce at least a portion of the supported transition metal catalyst to form a reduced transition metal catalyst, and (ii) hydrolyzing the reduced transition metal catalyst to form a reaction product comprising the alcohol compound and/or the carbonyl compound. Optionally, step (i) can comprise irradiating the hydrocarbon reactant and the supported transition metal catalyst in an oxidizing atmosphere.

In another aspect, a second process for converting a hydrocarbon reactant into an alcohol compound and/or a carbonyl compound can comprise (I) irradiating the hydrocarbon reactant and a supported transition metal catalyst comprising molybdenum, tungsten, vanadium, or a combination thereof, with a light beam at a wavelength in the UV-visible spectrum to reduce at least a portion of the supported transition metal catalyst to form a reduced transition metal catalyst, (II) subjecting the reduced transition metal catalyst to an oxidizing atmosphere, and (III) hydrolyzing the reduced transition metal catalyst to form a reaction product comprising the alcohol compound and/or the carbonyl compound.

Also provided herein are supported transition metal catalysts containing a solid support—e.g., a solid oxide such as silica-coated alumina, a chemically-treated solid oxide such as sulfated alumina, or a zeolite—and from 0.01 to 50 wt. % of a transition metal comprising molybdenum, tungsten, vanadium, or a combination thereof.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the catalysts, compositions, processes, or methods described herein are contemplated with or without explicit description of the particular combination. Additionally, unless explicitly recited otherwise, any aspect or feature disclosed herein can be combined to describe inventive catalysts, compositions, processes, or methods consistent with the present disclosure.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). Non-limiting examples of hydrocarbons include alkanes (linear, branched, and cyclic), alkenes (olefins), and aromatics, among other compounds. Herein, cyclics and aromatics encompass fused ring compounds such as bicyclics and polycyclics.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contacting" and "combining" are used herein to describe catalysts, compositions, processes, and methods in which the materials or components are contacted or combined together in any order, in any manner, and for any length of time, unless otherwise specified. For example, the materials or components can be blended, mixed, slurried, dissolved, reacted, treated, impregnated, compounded, or otherwise contacted or combined in some other manner or by any suitable method or technique.

"BET surface area" as used herein means the surface area as determined by the nitrogen adsorption Brunauer, Emmett, and Teller (BET) method according to ASTM D1993-91, and as described, for example, in Brunauer, S., Emmett, P. H., and Teller, E., "Adsorption of gases in multimolecular layers," J. Am. Chem. Soc., 60, 3, pp. 309-319, the contents of which are expressly incorporated by reference herein.

In this disclosure, while catalysts, compositions, processes, and methods are described in terms of "comprising" various components or steps, the catalysts, compositions, processes, and methods also can "consist essentially of" or "consist of" the various components or steps, unless stated otherwise.

The terms "a," "an," and "the" are intended to include plural alternatives, e.g., at least one. For instance, the disclosure of "a hydrocarbon reactant," "a solid oxide," etc., is meant to encompass one, or mixtures or combinations of more than one, hydrocarbon reactant, solid oxide, etc., unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical compound having a certain number of carbon atoms is disclosed or claimed, the intent is to disclose or claim individually every possible number that such a range could encompass, consistent with the disclosure herein. For example, the disclosure that a hydrocarbon reactant contains a $C_1$ to $C_{18}$ alkane compound, or in alternative language, an alkane compound having from 1 to 18 carbon atoms, as used herein, refers to a compound that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ alkane compound), and also including any combination of ranges between these two numbers (for example, a $C_2$ to $C_4$ alkane compound and a $C_{12}$ to $C_{16}$ alkane compound).

Similarly, another representative example follows for the amount of transition metal (molybdenum, tungsten, vanadium) on the supported transition metal catalyst consistent with aspects of this invention. By a disclosure that the amount of transition metal can be in a range from 0.1 to 15 wt. %, the intent is to recite that the amount of transition metal can be any amount in the range and, for example, can include any range or combination of ranges from 0.1 to 15 wt. %, such as from 0.2 to 10 wt. %, from 0.1 to 5 wt. %, or from 0.5 to 2.5 wt. %, and so forth. Likewise, all other ranges disclosed herein should be interpreted in a manner similar to these examples.

In general, an amount, size, formulation, parameter, range, or other quantity or characteristic is "about" or "approximately" whether or not expressly stated to be such. Whether or not modified by the term "about" or "approximately," the claims include equivalents to the quantities or characteristics.

Although any methods, devices, and materials similar or equivalent to those described herein can be used in the practice or testing of the invention, the typical methods, devices, and materials are herein described.

All publications and patents mentioned herein are incorporated herein by reference in their entirety for the purpose of describing and disclosing, for example, the constructs and methodologies that are described in the publications and patents, which might be used in connection with the presently described invention.

DETAILED DESCRIPTION OF THE INVENTION

The present invention is generally directed to the conversion of a hydrocarbon into an analogous alcohol compound and/or carbonyl compound. Unexpectedly, it was found that the combined use of a supported transition metal catalyst, light reduction, and hydrolysis can efficiently convert the hydrocarbon (e.g., an alkane) into the analogous alcohol compound and/or carbonyl compound, and beneficially, even at ambient temperature.

In some aspects, a step in the process of converting a hydrocarbon into an analogous alcohol compound and/or carbonyl compound is performed in an oxidizing atmosphere. It was expected, due to the well-known ability of oxygen to stop polymerization on transition metal based catalysts, that performing one step in these processes in an oxidizing atmosphere would result in no formation of alcohol/carbonyl products. However, instead, these processes provided significant increases in the molar yield of alcohol/carbonyl products (based on the transition metal present in the catalyst), as well as producing oxygenated oligomers.

Converting Hydrocarbons into Alcohols and Carbonyls

Disclosed herein are processes for converting a hydrocarbon reactant into an alcohol compound and/or a carbonyl compound. Carbonyl compounds, in this disclosure, encompass aldehydes, ketones, and carboxylic acids, among others. A first process for converting a hydrocarbon reactant into an alcohol compound and/or a carbonyl compound can comprise (i) irradiating the hydrocarbon reactant and a supported transition metal catalyst comprising molybdenum, tungsten, vanadium, or a combination thereof, with a light beam at a wavelength in the UV-visible spectrum to reduce at least a portion of the supported transition metal catalyst to form a reduced transition metal catalyst, and (ii) hydrolyzing the reduced transition metal catalyst to form a reaction product comprising the alcohol compound and/or the carbonyl compound. In step (i), at least a portion of the transition metal on the reduced transition metal catalyst can have at least one bonding site with a hydrocarboxy group (a —O-hydrocarbon group) such an alkoxy group, which upon hydrolysis in step (ii), can release an alcohol compound and/or carbonyl compound analog of the hydrocarbon compound. The reduced transition metal catalyst can have an average oxidation state less than that of the supported transition metal catalyst. In a variation of the first process, step (i) can comprise irradiating the hydrocarbon reactant and the supported transition metal catalyst in an oxidizing atmosphere.

A second process for converting a hydrocarbon reactant into an alcohol compound and/or a carbonyl compound can comprise (I) irradiating the hydrocarbon reactant and a supported transition metal catalyst comprising molybdenum, tungsten, vanadium, or a combination thereof, with a light beam at a wavelength in the UV-visible spectrum to reduce at least a portion of the supported transition metal catalyst to form a reduced transition metal catalyst, (II) subjecting the reduced transition metal catalyst to an oxidizing atmosphere, and (III) hydrolyzing the reduced transition metal catalyst to form a reaction product comprising the alcohol compound and/or the carbonyl compound.

Generally, the features of the first and second processes (e.g., the hydrocarbon reactant, the supported transition metal catalyst, the reduced transition metal catalyst, the light beam, the oxidizing atmosphere, and the conditions under which the irradiating step and the hydrolyzing step are conducted, among others) are independently described herein and these features can be combined in any combination to further describe the disclosed processes to produce alcohol compounds and/or carbonyl compounds. Moreover, additional process steps can be performed before, during, and/or after any of the steps in any of the processes disclosed herein, and can be utilized without limitation and in any combination to further describe these processes, unless stated otherwise. Further, any alcohol compounds and/or carbonyl compounds produced in accordance with the disclosed processes are within the scope of this disclosure and are encompassed herein.

A variety of hydrocarbon reactants can be used in the processes to form an alcohol compound and/or a carbonyl compound, inclusive of saturated aliphatic hydrocarbon compounds, unsaturated aliphatic hydrocarbon compounds, linear aliphatic hydrocarbon compounds, branched aliphatic hydrocarbon compounds, and cyclic aliphatic hydrocarbon compounds, as well as combinations thereof. Thus, the hydrocarbon reactant can comprise a linear alkane compound, a branched alkane compound, a cyclic alkane compound, or a combination thereof. Additionally or alternatively, the hydrocarbon reactant can comprise a linear olefin compound (e.g., an α-olefin), a branched olefin compound, a cyclic olefin compound, and the like, as well as combinations thereof. Additionally or alternatively, the hydrocarbon reactant can comprise an aromatic compound, such as benzene, toluene, and the like, as well as substituted versions thereof, and including combinations thereof.

Any suitable carbon number hydrocarbon can be used, such that the hydrocarbon reactant can comprise a $C_n$ hydrocarbon compound (and the alcohol compound often can comprise a $C_n$ alcohol compound, and the carbonyl compound often can comprise a $C_n$ carbonyl compound). In some aspects, the reaction product can contain higher carbon number alcohols and carbonyls, and in such circumstances, the hydrocarbon reactant can comprise a $C_n$ hydrocarbon compound, and the alcohol compound can comprise a $(C_{n+1})+$ alcohol compound and/or the carbonyl compound can comprise a $(C_{n+1})+$ carbonyl compound. As a particular example, when $C_n$ is a $C_2$ (n is equal to 2, such as for ethane or ethylene), then the term "$(C_{n+1})+$ alcohol compound" encompasses any $C_3$ and above ($C_4$, $C_5$, $C_6$, $C_7$, and so forth) alcohol compound and mixtures of $C_3$ and above ($C_4$, $C_5$, $C_6$, $C_7$, and so forth) alcohol compounds. The $(C_{n+1})+$ carbonyl compound would be interpreted similarly. While not being limited thereto, the integer n can range from 1 to 36 in one aspect, from 1 to 18 in another aspect, from 1 to 12 in yet another aspect, and from 1 to 8 in still another aspect.

Additionally or alternatively, the reaction product can contain lower carbon number alcohols and carbonyls, and in such circumstances, the hydrocarbon reactant can comprise a $C_n$ hydrocarbon compound, and the alcohol compound can comprise a $(C_{n-1})-$ alcohol compound and/or the carbonyl compound can comprise a $(C_{n-1})-$ carbonyl compound. As a particular example, when $C_n$ is a $C_5$ (n is equal to 5, such as for n-pentane or isopentane), then the term "$(C_{n-1})-$ carbonyl compound" encompasses any $C_4$ and below ($C_3$, $C_2$, and $C_1$) carbonyl compound and mixtures of $C_4$ and below ($C_3$, $C_2$, and $C_1$) carbonyl compounds. The alcohol compound would be interpreted similarly. While not being limited thereto, the integer n can range from 2 to 36 in one aspect, from 2 to 18 in another aspect, from 2 to 12 in yet another aspect, and from 2 to 8 in still another aspect.

Therefore, the hydrocarbon reactant can comprise any suitable carbon number alkane compound, for instance, a $C_1$ to $C_{36}$ alkane compound; alternatively, a $C_1$ to $C_{18}$ alkane compound; alternatively, a $C_1$ to $C_{12}$ alkane compound; or alternatively, a $C_1$ to $C_8$ alkane compound. If desired, the hydrocarbon reactant can contain a single alkane compound of relatively high purity, such as at least 90 wt. % of a single alkane compound, at least 95 wt. % of a single alkane compound, at least 98 wt. % of a single alkane compound, or at least 99 wt. % of a single alkane compound, and so forth. Alternatively, the hydrocarbon reactant can comprise a mixture of two or more hydrocarbon reactants, such as two or more alkane compounds in any relative proportions. Thus, the hydrocarbon reactant can comprise a mixture of $C_1$ to $C_{18}$ alkane compounds, a mixture of $C_1$ to $C_4$ alkane compounds, a mixture of $C_2$ to $C_6$ alkane compounds, a mixture of $C_6$ to $C_8$ alkane compounds, or a mixture of $C_{10}$ to $C_{14}$ alkane compounds, and the like.

Similarly, the hydrocarbon reactant can comprise any suitable carbon number olefin compound, for instance, a $C_2$ to $C_{36}$ olefin compound; alternatively, a $C_2$ to $C_{18}$ olefin compound; alternatively, a $C_2$ to $C_{12}$ olefin compound; or alternatively, a $C_2$ to $C_8$ olefin compound. As above, if desired, the hydrocarbon reactant can contain a single olefin compound of relatively high purity, such as at least 90 wt. % of a single olefin compound, at least 95 wt. % of a single olefin compound, at least 98 wt. % of a single olefin compound, or at least 99 wt. % of a single olefin compound, and so forth. Alternatively, the hydrocarbon reactant can comprise a mixture of two or more hydrocarbon reactants, such as two or more olefin compounds in any relative proportions. Thus, the hydrocarbon reactant can comprise a mixture of $C_2$ to $C_{36}$ olefin compounds, a mixture of $C_2$ to $C_{18}$ olefin compounds, a mixture of $C_2$ to $C_{12}$ olefin compounds, or a mixture of $C_2$ to $C_8$ olefin compounds, and the like.

Likewise, the hydrocarbon reactant can comprise any suitable carbon number aromatic compound, for instance, a $C_6$ to $C_{36}$ aromatic compound; alternatively, a $C_6$ to $C_{18}$ aromatic compound; alternatively, a $C_6$ to $C_{12}$ aromatic compound; or alternatively, a $C_6$ to $C_8$ aromatic compound.

As above, if desired, the hydrocarbon reactant can contain a single aromatic compound of relatively high purity, such as at least 90 wt. % of a single aromatic compound, at least 95 wt. % of a single aromatic compound, at least 98 wt. % of a single aromatic compound, or at least 99 wt. % of a single aromatic compound, and so forth. Alternatively, the hydrocarbon reactant can comprise a mixture of two or more hydrocarbon reactants, such as two or more aromatic compounds in any relative proportions. Thus, the hydrocarbon reactant can comprise a mixture of $C_6$ to $C_{36}$ aromatic compounds, a mixture of $C_6$ to $C_{18}$ aromatic compounds, a mixture of $C_6$ to $C_{12}$ aromatic compounds, or a mixture of $C_6$ to $C_8$ aromatic compounds, and the like.

Illustrative examples of alkane, olefin, and aromatic hydrocarbon reactants can include methane, ethane, propane, butane (e.g., n-butane or isobutane), pentane (e.g., n-pentane, neopentane, cyclopentane, or isopentane), hexane, heptane, octane, nonane, decane, undecane, dodecane, tridecane, tetradecane, pentadecane, hexadecane, heptadecane, octadecane, ethylene, propylene, 1-butene, 1-pentene, 2-pentene, 1-hexene, 1-heptene, 1-octene, 1-decene, 1-dodecene, 1-tetradecene, 1-hexadecene, 1-octadecene, cyclopentene, cyclohexene, benzene, toluene, ethylbenzene, xylene, styrene, mesitylene, and the like, as well as combinations thereof.

Thus, the hydrocarbon reactant can comprise a mixture of an aliphatic hydrocarbon and an aromatic hydrocarbon. In a non-limiting aspect, the hydrocarbon reactant can comprise methane; alternatively, ethane; alternatively, propane; alternatively, butane; alternatively, pentane; alternatively, hexane; alternatively, heptane; alternatively, octane; alternatively, nonane; alternatively, decane; alternatively, undecane; alternatively, dodecane; alternatively, tridecane; alternatively, tetradecane; alternatively, pentadecane; alternatively, hexadecane; alternatively, heptadecane; alternatively, octadecane; alternatively, ethylene; alternatively, propylene; alternatively, 1-butene; alternatively, 1-pentene; alternatively, 1-hexene; alternatively, 1-heptene; alternatively, 1-octene; alternatively, 1-decene; alternatively, 1-dodecene; alternatively, 1-tetradecene; alternatively, 1-hexadecene; alternatively, 1-octadecene; alternatively, cyclopentene; alternatively, cyclohexene; alternatively, benzene; alternatively, toluene; alternatively, ethylbenzene; alternatively, xylene; alternatively, styrene; or alternatively, mesitylene.

In an aspect, the hydrocarbon (alkane) reactant can comprise methane, ethane, propane, n-butane, isobutane, n-pentane, neopentane, isopentane, n-hexane, n-heptane, n-octane, n-decane, n-dodecane, and the like, or any combination thereof, while in another aspect, the hydrocarbon (alkane) reactant can comprise methane, ethane, propane, butane, pentane, hexane, and the like, or any combination thereof. In yet another aspect, the hydrocarbon (olefin) reactant can comprise ethylene, propylene, 1-butene, 1-pentene, 2-pentene, 1-hexene, 1-heptene, 1-octene, 1-decene, 1-dodecene, 1-tetradecene, 1-hexadecene, 1-octadecene, cyclopentene, cyclohexene, and the like, or any combination thereof, or alternatively, ethylene, propylene, 1-butene, 1-pentene, 1-hexene, 1-heptene, 1-octene, or any combination thereof. In still another aspect, the hydrocarbon (aromatic) reactant can comprise benzene, toluene, ethylbenzene, xylene, mesitylene, styrene, 4-phenyl-1-butene, and the like, or any combination thereof.

Generally, in the first process and the second process, the irradiating step can be performed under any conditions sufficient to accommodate the irradiation of the hydrocarbon reactant and the supported transition metal catalyst (e.g., comprising a transition metal having an oxo bond) with a light beam and to form the reduced transition metal catalyst (e.g., having a lower oxidation state). For instance, the relative amount (or concentration) of the hydrocarbon reactant to the amount of transition metal (in the supported transition metal catalyst) can alter the efficacy of the reduction process. In certain aspects, the molar ratio of the hydrocarbon reactant to the transition metal (in the supported transition metal catalyst) can be at least 0.25:1, at least 0.5:1, at least 1:1, at least 10:1, at least 100:1, at least 1000:1, or at least 10,000:1. Thus, a large excess of the hydrocarbon reactant can be used, and there is no particular limit as to the maximum amount of hydrocarbon reactant.

Likewise, when an oxidizing atmosphere is used, the molar ratio of elemental oxygen or other oxidizing agent to transition metal (of the supported transition metal catalyst, or of the reduced transition metal catalyst, as the context requires for the respective process) is not particularly limited, but often can be at least 0.25:1, at least 0.5:1, at least 1:1, at least 10:1, at least 100:1, at least 1000:1, or at least 10,000:1. Thus, a large excess of the elemental oxygen or other oxidizing agent can be used, and there is no particular limit as to the maximum amount of elemental oxygen or other oxidizing agent in the oxidizing atmosphere. For instance, a large molar excess of air can be used in these processes.

In the first and second processes, the temperature and pressure of the irradiating step can be such that the hydrocarbon reactant remains a liquid throughout reduction of the supported transition metal catalyst in one aspect, and the hydrocarbon remains a gas throughout reduction of the supported transition metal catalyst in another aspect. Advantageously, it was found that reducing supported transition metal compounds at lower temperatures than those typically required to reduce high valence transitional metal species using heat and not light, was possible by the irradiating steps disclosed herein. In certain aspects, the irradiating step can be conducted at a temperature of less than 200° C., less than 100° C., less than 70° C., less than 40° C., from 0° C. to 200° C., from −100° C. to 100° C., from 0° C. to 100° C., or from 10° C. to 40° C., and can produce a reduced transition metal catalyst. These temperature ranges also are meant to encompass circumstances where the irradiation is performed at a series of different temperatures, instead of at a single fixed temperature, falling within the respective temperature ranges, wherein at least one temperature is within the recited ranges.

The irradiating step can be further characterized by an amount of time that the hydrocarbon reactant and supported transition metal catalyst are exposed to the light beam, e.g., an exposure time. Without being bound by theory, it is believed that exposure to the light beam in the presence of the hydrocarbon reactant is responsible for the reduction of the supported transition metal catalyst, and therefore it follows that the exposure time must be sufficient to allow this transformation to occur, whether the transformation occurs very rapidly or very slowly. Thus, in certain aspects, and not being limited thereto, the exposure time can be in a range from 15 sec to 48 hr, from 15 sec to 24 hr, from 1 hr to 8 hr, from 15 min to 4 hr, from 1 min to 6 hr, from 5 min to 1 hr, from 10 min to 2 hr, from 1 min to 1 hr, or from 1 min to 15 min. As one of skill in the art would recognize, the exposure time can vary based on the intensity of the light beam, the wavelength(s) of the light beam, and so forth. Agitation, mixing, or other suitable technique can be used to ensure that the mixture of the supported transition metal catalyst (e.g., particles) and the hydrocarbon reactant is uniformly contacted and/or exposed to the light beam irradiation.

The supported transition metal catalyst and the hydrocarbon reactant can be continuously subjected to irradiation (for the entirety of the exposure time), or the irradiation can be pulsed (such that the total of the pulses equates to the exposure time, e.g., sixty 1-sec pulses equates to a 60-sec exposure time). Combinations of periods of continuous irradiation and pulsed irradiation can be utilized, if desired.

In the disclosed processes, irradiation of a supported transition metal catalyst with a light beam in the UV-visible spectrum, in the presence of a hydrocarbon reactant, results in a transition metal catalyst with a reduced oxidation state (e.g., a reduced transition metal catalyst). A wide range of wavelengths, light sources, and intensities can be used, as long as these wavelengths, light sources, and intensities are sufficient to reduce at least a portion of the high valence transition metal species present in the supported transition metal catalyst. In certain aspects, for instance, the light can be derived from any suitable source, such as from sunlight, a fluorescent white light, an LED diode, and/or a UV lamp. The distance from non-sunlight sources can be varied as needed (e.g., minimized) to increase the effectiveness of the irradiation.

The wavelength of the light can be any in the range of UV-visible light. In certain aspects, the wavelength of the light beam can be a single wavelength, or more than one wavelength, such as a range of wavelengths. For instance, the wavelength of the light beam can be a range of wavelengths spanning at least 25 nm, at least 50 nm, at least 100 nm, at least 200 nm, or at least 300 nm. In one aspect, the wavelength of the light beam can comprise a single wavelength or a range of wavelengths in the UV spectrum, in the visible spectrum (from 380 nm to 780 nm), or both. In another aspect, the wavelength of the light beam can comprise a single wavelength or a range of wavelengths in the 200 nm to 750 nm range. Yet, in another aspect, the wavelength of the light beam can comprise a single wavelength or a range of wavelengths in the 300 to 750 nm range, the 350 nm to 650 nm range, the 300 nm to 600 nm range, the 300 nm to 500 nm range, or the 400 nm to 500 nm range. In other aspects, the wavelength of the light beam can comprise a single wavelength or a range of wavelengths below 600 nm, below 525 nm, or below 500 nm; additionally or alternatively, above 300 nm, above 350 nm, above 400 nm, or above 450 nm. Beneficially, blue light and UV light sources are typically more effective, thus the wavelength of the light beam can comprise a single wavelength or a range of wavelengths below 475 nm; alternatively, below 450 nm; alternatively, below 430 nm; or alternatively, below 420 nm; and additionally or alternatively, above 350 nm; alternatively, above 370 nm; alternatively, above 380 nm; or alternatively, above 400 nm.

The light beam of the irradiating step also can be characterized by its intensity (e.g., the total amount of light emitted from a source). In certain aspects, the light beam can have an intensity of at least 500 lumens, at least 1,000 lumens, at least 2,000 lumens at least 5,000 lumens, at least 10,000 lumens, at least 20,000 lumens, at least 50,000 lumens, or at least 100,000 lumens. Thus, there may not be an upper limit on the intensity of the light source. Alternatively, the light beam can have an intensity in a range from 50 to 50,000 lumens, from 50 to 10,000 lumens, from 100 to 5,000 lumens, or from 500 to 2,000 lumens. Additionally, the light beam can be characterized by the amount of light reaching the hydrocarbon reactant and supported transition metal catalyst, i.e., the flux. In certain aspects, the hydrocarbon reactant and the supported transition metal catalyst (comprising molybdenum, tungsten, and/or vanadium) can be irradiated by at least 100 lux, at least 500 lux, at least 1000 lux, at least 2000 lux, at least 5000 lux, at least 10,000 lux, at least 20,000 lux, at least 50,000 lux, at least 100,000 lux, or in a range from 10,000 to 1,000,000 lux, from 10,000 to 250,000 lux, from 10,000 to 100,000 lux, from 20,000 to 200,000 lux, from 20,000 to 100,000 lux, from 50,000 to 500,000 lux, or from 50,000 to 200,000 lux. Additionally or alternatively, in certain aspects, the hydrocarbon reactant and the supported transition metal catalyst can be irradiated with a light beam having a power of at least 50 watts, at least 100 watts, at least 200 watts, at least 500 watts, at least 1,000 watts, or at least 2,000 watts.

Any suitable reactor or vessel can be used to form the alcohol compound and/or the carbonyl compound, non-limiting examples of which can include a flow reactor, a continuous reactor, a packed bed reactor, a fluidized bed reactor, and a stirred tank reactor, including more than one reactor in series or in parallel, and including any combination of reactor types and arrangements.

In one aspect, the hydrocarbon reactant can be in a gas phase during the irradiating step. In another aspect, the hydrocarbon reactant can be in a liquid phase during the irradiating step. In another aspect, the disclosed processes can comprise irradiating a slurry (e.g., a loop slurry) of the solid supported transition metal catalyst in the hydrocarbon reactant. In yet another aspect, the disclosed processes can comprise contacting the hydrocarbon reactant with a fluidized bed of the solid supported transition metal catalyst, and irradiating while contacting (fluidizing). In still another aspect, the disclosed processes can comprise contacting the hydrocarbon reactant (e.g., in the gas phase or in the liquid phase) with a fixed bed of the solid supported transition metal catalyst, and irradiating while contacting. As a skilled artisan would recognize, there are other methods for contacting the hydrocarbon reactant and the solid supported transition metal catalysts and irradiating, and the disclosed processes are not limited solely to those disclosed herein. For instance, the hydrocarbon reactant and the supported transition metal catalyst can be mixed or contacted in a stirred tank, and irradiated while being mixed in the stirred tank.

Any suitable pressure can be used to contact the hydrocarbon reactant and the supported catalyst and to form the reduced transition metal catalyst, and such can depend upon the carbon number of the hydrocarbon reactant (and its boiling point), the type of reactor configuration and desired mode for contacting the hydrocarbon reactant with the (solid) supported transition metal catalyst, among other considerations.

Often, the process for forming the reduced transition metal catalyst (and subsequently, the alcohol and/or carbonyl compound) can be a flow process and/or a continuous process. In such circumstances, the hydrocarbon reactant-supported transition metal catalyst contact time (or reaction time) can be expressed in terms of weight hourly space velocity (WHSV)—the ratio of the weight of the hydrocarbon reactant which comes in contact with a given weight of the supported transition metal catalyst per unit time (units of g/g/hr, or $hr^{-1}$).

While not limited thereto, the WHSV employed for the disclosed processes can have a minimum value of 0.01 $hr^{-1}$, 0.02 $hr^{-1}$, 0.05 $hr^{-1}$, 0.1 $hr^{-1}$, 0.25 $hr^{-1}$, or 0.5 $hr^{-1}$; or alternatively, a maximum value of 500 $hr^{-1}$, 400 $hr^{-1}$, 300 $hr^{-1}$, 100 $hr^{-1}$, 50 $hr^{-1}$, 10 $hr^{-1}$, 5 $hr^{-1}$, 2 $hr^{-1}$, or 1 $hr^{-1}$.

Generally, the WHSV can be in a range from any minimum WHSV disclosed herein to any maximum WHSV disclosed herein. In a non-limiting aspect, the WHSV can be in a range from 0.01 hr$^{-1}$ to 500 hr$^{-1}$; alternatively, from 0.01 hr$^{-1}$ to 10 hr$^{-1}$; alternatively, from 0.01 hr$^{-1}$ to 1 hr$^{-1}$; alternatively, from 0.02 hr$^{-1}$ to 400 hr$^{-1}$; alternatively, from 0.02 hr$^{-1}$ to 50 hr$^{-1}$; alternatively, from 0.05 hr$^{-1}$ to 300 hr$^{-1}$; alternatively, from 0.05 hr$^{-1}$ to 5 hr$^{-1}$; alternatively, from 0.1 hr$^{-1}$ to 400 hr$^{-1}$; alternatively, from 0.25 hr$^{-1}$ to 50 hr$^{-1}$; alternatively, from 0.25 hr$^{-1}$ to 2 hr$^{-1}$; alternatively, from 0.5 hr$^{-1}$ to 400 hr$^{-1}$; alternatively, from 0.5 hr$^{-1}$ to 5 hr$^{-1}$; or alternatively, from 0.5 hr$^{-1}$ to 2 hr$^{-1}$. Other WHSV ranges are readily apparent from this disclosure.

Referring now to the second process, step (II) is directed to subjecting the reduced transition metal catalyst to an oxidizing atmosphere. This step of subjecting the reduced transition metal catalyst to an oxidizing atmosphere generally can be performed, independently, under the same temperature, pressure, time, and method of contacting (e.g., fixed bed or fluidized bed) conditions described herein for the irradiating steps (step (i) of the first process and step (I) of the second process).

The oxidizing atmosphere in the first process and the second process is not particular limited. Typical materials used to create the oxidizing atmosphere include, but are not limited to, oxygen, air, a mixture of air and an inert gas (such as nitrogen), a mixture of oxygen and an inert gas, NO, $NO_2$, $N_2O$, ozone, a halide oxide, $H_2O_2$, an organic peroxide, and the like, as well as combinations thereof. For convenience, air is often used, and thus the respective transition metal catalyst in the first process and the second process can be simply subjected to or exposed to air under any suitable conditions.

Referring now to the hydrolyzing steps, in which the reduced transition metal catalyst (e.g., with at least a portion of the transition metal on the reduced transition metal catalyst having at least one bonding site with a hydrocarboxy group) is hydrolyzed to form a reaction product comprising the alcohol compound and/or the carbonyl compound. Generally, the temperature, pressure, and time features of the hydrolyzing step can be the same as those disclosed herein for the irradiating step, although not limited thereto. For example, the hydrolyzing step can be conducted at a temperature of less than 200° C., less than 100° C., less than 70° C., less than 40° C., from 0° C. to 200° C., from 0° C. to 100° C., or from 10° C. to 40° C., and can result in the formation of a reaction product containing the alcohol compound and/or the carbonyl compound. These temperature ranges also are meant to encompass circumstances where the hydrolyzing step is performed at a series of different temperatures, instead of at a single fixed temperature, falling within the respective temperature ranges, wherein at least one temperature is within the recited ranges.

While not limited thereto, the hydrolyzing step can comprise contacting the reduced transition metal catalyst with a hydrolysis agent. Illustrative and non-limiting examples of suitable hydrolysis agents can include water, steam, an alcohol agent, an acid agent, an alkaline agent, and the like, as well as combinations thereof. Thus, mixtures of water and various alcohol agents, such as $C_1$-$C_4$ alcohols (and/or acid agents, such as hydrochloric acid, sulfuric acid, acetic acid, ascorbic acid, and the like; and/or alkaline agents, such as sodium hydroxide, ammonium hydroxide, and the like) in any relative proportions can be used as the hydrolysis agent. Thus, the pH of the hydrolysis agent(s) can range from acid to neutral to basic pH values, generally encompassing a pH range from 1 (or less) to 13-13.5.

Optionally, the hydrolysis agent can further comprise any suitable reducing agent, and representative reducing agents include ascorbic acid, iron (II) reducing agents, zinc reducing agents, and the like, as well as combinations thereof. Often, the reducing agent can comprise sodium bisulfite, sodium thiosulfate, sodium sulfide, ascorbic acid, ferrous (II) ions, and the like, or any combination thereof. These are sometimes useful for preventing unwanted secondary oxidations by unreacted transition metal. Further, they also can be used to tailor the product range by increasing selectivity. For example, in some aspects, adding reducing agents to the hydrolysis agent can eliminate all carbonyl products and instead produce only alcohol products. For instance, a reducing agent can be added in the final quench solution in order to produce more alcohol products and less carbonyl products (e.g., to prevent secondary oxidation of the alcohols formed).

As disclosed herein, the reaction product can comprise an alcohol compound and/or a carbonyl compound, which can be an analog of the hydrocarbon reactant. Thus, typical alcohol compounds that can be synthesized using the processes disclosed herein can include, for instance, methanol, ethanol, isopropanol, butanols, pentanols, hexanols, heptanols, octanols, nonanols, decanols, undecanols, dodecanols, tridecanols, tetradecanols, pentadecanols, hexadecanols, heptadecanols, octadecanols, benzyl alcohol, phenols, xylenols, and the like, as well as combinations thereof. Herein, an alcohol compound encompasses monoalcohol compounds as well as diol compounds (e.g., ethanediol and hexanediols). Thus, the alcohol compound can comprise a diol, an allylic alcohol, a phenol, and the like, as well as any combination thereof.

In addition to or in lieu of the alcohol compound, the reaction product can comprise a carbonyl compound, such as an aldehyde compound, a ketone compound, or a carboxylic acid compound, as well as any combination of aldehyde, ketone, and carboxylic acid compounds. Thus, enols are encompassed herein, since the reaction product can comprise an alcohol compound, a carbonyl compound, or both. As an example, representative carboxylic acids that can be synthesized using the processes disclosed herein can include, for instance, formic acid, acetic acid, propionic acid, butanoic acid, pentanoic acid, hexanoic acid, heptanoic acid, octanoic acid, and the like, as well as combinations thereof. In a particular aspect, the reaction product can comprise (or consist essentially of, or consist of) acetic acid.

In some aspects, the alcohol or carbonyl product can contain unsaturation. For example, the carbon(s) adjacent to the alcohol or carbonyl group can contain a double bond. While not wishing to be bound by theory, it is believed that the allyl C—H bond is particularly susceptible to being attacked by the transition metal species. Thus, when the reductant hydrocarbon has a double bond, a typical alcohol product, and often among the most abundant, contains the —OH group on the adjacent allyl carbon. The alcohol compound in some aspects, therefore, can be an allylic alcohol such as a $C_4$-$C_8$ allylic alcohol. Non-limiting examples of allylic alcohols that can be prepared herein include 1-hexen-3-ol, 2-hexen-1-ol, 1-penten-3-ol, 2-penten-1-ol, 1-cyclohexen-3-ol, and the like, as well as combinations thereof.

The processes described herein result in an unexpectedly high conversion of the hydrocarbon reactant and/or yield to the alcohol compound (or carbonyl compound). In one aspect, the minimum conversion (or yield) can be at least 2 wt. %, at least 5 wt. %, at least 10 wt. %, at least 15 wt. %, or at least 25 wt. % of the feedstock hydrocarbon. Additionally, the maximum conversion (or yield) can be 50 wt. %, 70 wt. %, 80 wt. %, 90 wt. %, 95 wt. %, or 99 wt. %, and can approach 100% conversion of the hydrocarbon reactant (or yield of the alcohol compound, or yield of the carbonyl compound). Generally, the conversion (or yield) can be in a range from any minimum conversion (or yield) disclosed herein to any maximum conversion (or yield) disclosed herein. Non-limiting ranges of conversion (or yield) can include from 5 wt. % to 99 wt. %, from 10 wt. % to 95 wt. %, or from 15 wt. % to 70 wt. %. For conversion, the percentages are the amount of the hydrocarbon reactant converted based on the initial amount of the hydrocarbon reactant. The yield values are weight percentages, and are based on the weight of the alcohol compound (or carbonyl compound) produced to the weight of hydrocarbon reactant. In some aspects, these conversions (or yields) can be achieved in a batch process, while in other aspects, these conversions (or yields) can be achieved in a flow or continuous process, such as, for example, a single pass or multiple passes through a reactor (e.g., a fixed bed reactor). Often, the conversion and yield can be manipulated by varying the ratio of reductant hydrocarbon feed to the amount of transition metal, the amount of oxygen in the oxidizing atmosphere, and by varying other reaction conditions such as time, temperature, and irradiation.

Also unexpectedly, continuous flow processes for producing the alcohol compound and/or carbonyl compound in accordance with this invention have unexpectedly high single pass conversions of the hydrocarbon reactant (or single pass yields to the desired alcohol or carbonyl compound). In one aspect, the minimum single pass conversion (or yield) can be at least 2 wt. %, at least 5 wt. %, at least 10 wt. %, at least 15 wt. %, or at least 25 wt. %. Additionally, the maximum single pass conversion (or yield) can be 50 wt. %, 70 wt. %, 80 wt. %, 90 wt. %, 95 wt. %, or 99 wt. %, and can approach 100% conversion of the hydrocarbon reactant (or yield of the alcohol compound, or yield of the carbonyl compound), depending upon the reaction conditions. Generally, the single pass conversion (or yield) can be in a range from any minimum single pass conversion (or yield) disclosed herein to any maximum single pass conversion (or yield) disclosed herein. Non-limiting ranges of single pass conversion (or yield) can include from 5 wt. % to 99 wt. %, from 10 wt. % to 95 wt. %, or from 15 wt. % to 70 wt. %.

In the first and second processes, the yield of the alcohol compound (or carbonyl compound) also can be characterized based on the amount of transition metal (of the supported transition metal catalyst). For instance, the molar ratio (molar yield) of the alcohol compound (or carbonyl compound) based on the moles of transition metal can be at least 0.01, at least 0.05, at least 0.1, or at least 0.25 moles, at least 0.5 moles, or at least 0.75 moles. While not limited thereto, the yield in moles of product per mole of transition metal often can be up to 10 moles, up to 8 moles, up to 5 moles, up to 3 moles, up to 2 moles, up to 1.5 moles, or up to 1 mole of the alcohol compound (or carbonyl compound) per mole of transition metal. If more than one alcohol compound and/or carbonyl compound is/are produced, then this ratio represents the total moles of alcohol and/or carbonyl compounds produced per mole of transition metal.

The processes to produce the alcohol compounds and/or carbonyl compounds disclosed herein typically can result in—after hydrolysis—a crude reaction mixture containing residual hydrocarbon reactant (e.g., alkane and/or olefin), a desired alcohol compound and/or carbonyl compound (e.g., aldehyde and/or carboxylic acid, such as acetic acid), solvent (if used), and by-products. In many instances, it can be desirable to isolate or separate at least a portion (and in some cases, all) of the hydrocarbon reactant from the reaction product after the hydrolyzing step. This can be accomplished using any suitable technique, which can include but is not limited to, extraction, filtration, evaporation, or distillation, as well as combinations of two or more of these techniques. In particular aspects of this invention, the isolating or separating step utilizes distillation at any suitable pressure (one or more than one distillation column can be used).

Additionally or alternatively, the processes disclosed herein can further comprise a step of separating at least a portion (and in some cases, all) of the alcohol compound (or carbonyl compound) from the reaction product, and any suitable technique can be used, such as extraction, filtration, evaporation, distillation, or any combination thereof. Additionally or alternatively, the processes disclosed herein can further comprise a step of separating at least a portion (and in some cases, all) of the reduced transition metal catalyst from the reaction product after hydrolyzing, and as above, any suitable technique(s) can be used.

Optionally, certain components of the reaction product—such as the hydrocarbon reactant—can be recovered and recycled to the reactor. In such instances, at least a portion (and in some cases, all) of the hydrocarbon reactant can be recycled and contacted with supported transition metal catalyst again, such that the overall conversion of the hydrocarbon product is increased after multiple contacts with the supported transition metal catalyst (or multiple passes through the reactor containing the supported transition metal catalyst).

If desired, the processes disclosed herein can further comprise a step of calcining at least a portion (and in some cases, all) of the reduced transition metal catalyst to regenerate the supported transition metal catalyst. Any suitable calcining conditions can be used, for instance, subjecting the at least a portion of the reduced transition metal catalyst to an oxidizing atmosphere at any suitable peak temperature and time conditions, such as a peak temperature from 300° C. to 1000° C., from 500° C. to 900° C., or from 550° C. to 870° C., for a time period of from 1 min to 24 hr, from 1 hr to 12 hr, or from 30 min to 8 hr.

The calcining step can be conducted using any suitable technique and equipment, whether batch or continuous. For instance, the calcining step can be performed in a belt calciner or, alternatively, a rotary calciner. In some aspects, the calcining step can be performed in a batch or continuous calcination vessel comprising a fluidized bed. As would be recognized by those of skill in the art, other suitable techniques and equipment can be employed for the calcining step, and such techniques and equipment are encompassed herein.

Optionally, the first and second processes disclosed herein can further comprise a step of calcining the supported transition metal catalyst (containing molybdenum, tungsten, and/or vanadium) prior to the irradiating step. Any suitable calcining conditions can be used, for instance, subjecting the supported transition metal catalyst to an oxidizing atmosphere (in some aspects, an inert atmosphere can be used) at any suitable peak temperature and time conditions, such as a peak temperature from 200° C. to 1000° C., from 300° C. to 800° C., or from 450° C. to 750° C., for a time period of from 1 min to 24 hr, from 1 hr to 12 hr, or from 30 min to 8 hr.

Transition Metal Catalysts

Generally, the disclosed processes are applicable to the reduction of a supported transition metal catalyst, and are not limited to the reduction of any particular type of supported transition metal catalyst. Often, the supported transition metal catalyst can be described as comprising a transition metal having an oxo bond (transition metal =O bond). Additionally or alternatively, the supported transition metal catalyst can be described as comprising a transition metal in at least a +3 oxidation state. Additionally or alternatively, the supported transition metal catalyst can be described as comprising a transition metal in one of its uppermost two oxidation states. Note that the transition metal can have more than one oxo bond. In aspects of this invention, the supported transition metal catalyst can comprise molybdenum, tungsten, vanadium, or a combination thereof (e.g., two or more transition metals can be present on the supported transition metal catalyst); alternatively, molybdenum; alternatively, tungsten; or alternatively, vanadium.

While not limited thereto, supported transition metal catalysts contemplated herein encompass those prepared by contacting a support with a transition metal-containing compound and calcining in an oxidizing atmosphere to form a supported transition metal catalyst. In these aspects, the transition metal can be impregnated during, or prior to, the calcination step, which can be conducted at a variety of temperatures and time periods, and can be generally selected to convert all or a portion of the transition metal to at least a +3 oxidation state and/or to one of its uppermost two oxidation states. The irradiation methods disclosed herein can comprise reducing at least a portion of the higher oxidation state transition metal species to a reduced oxidation state (or oxidation states) in the reduced transition metal catalyst.

Any suitable transition metal-containing compound (or transition metal precursor) can be used as a transition metal component to prepare the supported catalyst. In some aspects, it can be beneficial for the transition metal-containing compound to be soluble in a hydrocarbon solvent during preparation of the supported catalyst, while in other aspects, it can be beneficial for the transition metal-containing compound to be soluble in water during preparation of the supported catalyst.

Various solid supports can be used for the supported transition metal catalyst (and the reduced transition metal catalyst), such as conventional solid oxides and zeolites. Generally, the solid oxide can comprise oxygen and one or more elements selected from Group 2, 3, 4, 5, 6, 7, 8, 9, 10, 11, 12, 13, 14, or 15 of the periodic table, or comprise oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the solid oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr. Illustrative examples of solid oxide materials or compounds that can be used as solid support can include, but are not limited to, $Al_2O_3$, $B_2O_3$, $BeO$, $Bi_2O_3$, $CdO$, $Co_3O_4$, $Cr_2O_3$, $CuO$, $Fe_2O_3$, $Ga_2O_3$, $La_2O_3$, $Mn_2O_3$, $MoO_3$, $NiO$, $P_2O_5$, $Sb_2O_5$, $SiO_2$, $SnO_2$, $SrO$, $ThO_2$, $TiO_2$, $V_2O_5$, $WO_3$, $Y_2O_3$, $ZnO$, $ZrO_2$, and the like, including mixed oxides thereof, and combinations thereof.

The solid oxide can encompass oxide materials such as silica, "mixed oxide" compounds thereof such as silica-titania, and combinations or mixtures of more than one solid oxide material. Mixed oxides such as silica-titania can be single or multiple chemical phases with more than one metal combined with oxygen to form the solid oxide. Examples of mixed oxides that can be used as solid oxide include, but are not limited to, silica-alumina, silica-coated alumina, silica-titania, silica-zirconia, alumina-titania, alumina-zirconia, zinc-aluminate, alumina-boria, alumina borate, silica-boria, aluminum phosphate, aluminophosphate, aluminophosphate-silica, titania-zirconia, and the like, or a combination thereof. In some aspects, the solid support can comprise silica, silica-alumina, silica-coated alumina, silica-titania, silica-titania-magnesia, silica-zirconia, silica-magnesia, silica-boria, aluminophosphate-silica, alumina, alumina borate, and the like, or any combination thereof. Silica-coated aluminas are encompassed herein; such oxide materials are described in, for example, U.S. Pat. Nos. 7,884,163 and 9,023,959, incorporated herein by reference in their entirety.

The percentage of each oxide in a mixed oxide can vary depending upon the respective oxide materials. As an example, a silica-alumina (or silica-coated alumina) typically has an alumina content from 5 wt. % to 95 wt. %. According to one aspect, the alumina content of the silica-alumina (or silica-coated alumina) can be from 5 wt. % alumina 50 wt. % alumina, or from 8 wt. % to 30 wt. % alumina. In another aspect, high alumina content silica-aluminas (or silica-coated aluminas) can be employed, in which the alumina content of these materials typically ranges from 60 wt. % alumina to 90 wt. % alumina, or from 65 wt. % alumina to 80 wt. % alumina.

In one aspect, the solid oxide can comprise silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, or a combination thereof; alternatively, silica-alumina; alternatively, silica-coated alumina; alternatively, silica-titania; alternatively, silica-zirconia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; or alternatively, titania-zirconia.

In another aspect, the solid oxide can comprise silica, alumina, titania, thoria, stania, zirconia, magnesia, boria, zinc oxide, a mixed oxide thereof, or any mixture thereof. In yet another aspect, the solid support can comprise silica, alumina, titania, or a combination thereof; alternatively, silica; alternatively, alumina; alternatively, titania; alternatively, zirconia; alternatively, magnesia; alternatively, boria; or alternatively, zinc oxide. In still another aspect, the solid oxide can comprise silica, alumina, silica-alumina, silica-coated alumina, aluminum phosphate, aluminophosphate, heteropolytungstate, titania, zirconia, magnesia, boria, zinc oxide, silica-titania, silica-yttria, silica-zirconia, alumina-titania, alumina-zirconia, zinc-aluminate, alumina-boria, silica-boria, aluminophosphate-silica, titania-zirconia, and the like, or any combination thereof.

In circumstances in which the supported transition metal catalyst and the reduced transition metal catalyst comprise a silica-titania, any suitable amount of titanium can be present, including from 0.1 to 20 wt. %, from 0.5 to 15 wt. %, from 1 to 10 wt. %, or from 1 to 6 wt. % titanium, based on the total weight of the supported catalyst and the reduced catalyst.

Consistent with certain aspects of this invention, the supported transition metal catalyst and the reduced transition metal catalyst can comprise a chemically-treated solid oxide as the support, and where the chemically-treated solid oxide comprises a solid oxide (any solid oxide disclosed herein)

treated with an electron-withdrawing anion (any electron withdrawing anion disclosed herein). The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, molybdate, and the like, including mixtures and combinations thereof. In addition, other ionic or non-ionic compounds that serve as sources for these electron-withdrawing anions also can be employed.

It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The chemically-treated solid oxide generally can contain from 1 wt. % to 30 wt. % of the electron-withdrawing anion, based on the weight of the chemically-treated solid oxide. In particular aspects provided herein, the chemically-treated solid oxide can contain for instance, from 1 to 20 wt. %, from 2 wt. % to 20 wt. %, from 3 wt. % to 20 wt. %, from 2 wt. % to 15 wt. %, from 1 wt. % to 10 wt. %, from 2 wt. % to 10 wt. %, or from 3 wt. % to 10 wt. %, of the electron-withdrawing anion, based on the total weight of the chemically-treated solid oxide.

In an aspect, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, and the like, as well as any mixture or combination thereof.

In another aspect, the chemically-treated solid oxide employed in the supported transition metal catalyst and the reduced transition metal catalyst and the processes described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, sulfated silica-coated alumina, and the like, as well as combinations thereof. Additional information on chemically-treated solid oxide can be found in, for instance, U.S. Pat. Nos. 7,294,599, 7,601,665, 7,884,163, 8,309,485, 8,623,973, and 8,703,886, which are incorporated herein by reference in their entirety.

Consistent with certain aspects of this invention, the supported transition metal catalyst and the reduced transition metal catalyst can comprise a zeolite as the support, i.e., a transition metal supported zeolite. Any suitable zeolite can be used, for instance, large pore and medium pore zeolites. Large pore zeolites often have average pore diameters in a range of from 7 Å to 12 Å, and non-limiting examples of large pore zeolites include L-zeolite, Y-zeolite, mordenite, omega zeolite, beta zeolite, and the like. Medium pore zeolites often have average pore diameters in a range of from 5 Å to 7 Å. Combinations of zeolitic supports can be used.

Additional representative examples of zeolites that can be used in the supported transition metal catalyst and the reduced transition metal catalyst include, for instance, a ZSM-5 zeolite, a ZSM-11 zeolite, a EU-1 zeolite, a ZSM-23 zeolite, a ZSM-57 zeolite, an ALPO4-11 zeolite, an ALPO4-41 zeolite, a Ferrierite framework type zeolite, and the like, or any combination thereof.

In the supported transition metal catalyst and the reduced transition metal catalyst, the zeolite can be bound with a support matrix (or binder), non-limiting examples of which can include silica, alumina, magnesia, boria, titania, zirconia, various clays, and the like, including mixed oxides thereof, as well as mixtures thereof. For example, the supported transition metal catalyst and the reduced transition metal catalyst support can comprise a binder comprising alumina, silica, a mixed oxide thereof, or a mixture thereof. The zeolite can be bound with the binder using any method known in the art. While not being limited thereto, the supported transition metal catalyst and the reduced transition metal catalyst can comprise a zeolite and from 3 wt. % to 35 wt. % binder; alternatively, from 5 wt. % to 30 wt. % binder; or alternatively, from 10 wt. % to 30 wt. % binder. These weight percentages are based on the total weight of the supported transition metal catalyst or the reduced transition metal catalyst.

The amount of transition metal in the supported transition metal catalyst and the reduced transition metal catalyst also is not particularly limited. However, the amount of transition metal in the supported transition metal catalyst and the reduced transition metal catalyst typically ranges from 0.01 to 50 wt. %; alternatively, from 0.01 to 20 wt. %; alternatively, from 0.01 to 10 wt. %; alternatively, from 0.05 to 15 wt. %; alternatively, from 0.1 to 15 wt. %; alternatively, from 0.2 to 10 wt. %; alternatively, from 0.1 to 5 wt. %; alternatively, from 0.5 to 30 wt. %; or alternatively, from 0.5 to 2.5 wt. %. These weight percentages are based on the amount of transition metal relative to the total weight of the supported transition metal catalyst or the reduced transition metal catalyst. While not wishing to be bound by theory, it is believed that lower transition metal loadings (e.g., 1 wt. % and less) can result in higher selectivity to a particular alcohol compound (or carbonyl compound), while higher transition metal loadings (e.g., 5-15 wt. % and above) can result in higher alcohol and/or carbonyl yields per gram of catalyst.

The irradiation of the supported transition metal catalyst—in the presence of the hydrocarbon reactant—ordinarily results in at least 10 wt. %, at least 20 wt. %, at least 40 wt. %, at least 60 wt. %, at least 80 wt. %, or at least 90 wt. %, of the supported transition metal catalyst being reduced or converted to form the reduced transition metal catalyst in the first and second processes.

The total pore volume of the supported transition metal catalyst and the reduced transition metal catalyst also is not particularly limited. For instance, the supported transition metal catalyst and the reduced transition metal catalyst can have a total pore volume in a range from 0.1 to 5 mL/g, from 0.15 to 5 mL/g, from 0.1 to 3 mL/g, from 0.5 to 2.5 mL/g, from 0.15 to 2 mL/g, from 0.3 to 1.5 mL/g, or from 0.5 to 1.0 mL/g. Likewise, the surface area of the supported transition metal catalyst and the reduced transition metal catalyst is not limited to any particular range. Generally, however, the supported transition metal catalyst and the reduced transition metal catalyst can have a BET surface area in a range from 50 to 2000 m$^2$/g, from 50 to 700 m$^2$/g, from 50 to 400 m$^2$/g, from 100 to 1200 m$^2$/g, from 150 to 525 m$^2$/g, or from 200 to 400 m$^2$/g.

The supported transition metal catalyst and the reduced transition metal catalyst can have any suitable shape or form, and such can depend on the type of process that is employed to convert the hydrocarbon reactant into the alcohol compound and/or carbonyl compound (e.g., fixed bed versus fluidized bed). Illustrative and non-limiting shapes and forms include powder, round or spherical (e.g., a sphere), ellipsoidal, pellet, bead, cylinder, granule (e.g., regular and/or irregular), trilobe, quadrilobe, ring, wagon wheel, monolith, and the like, as well as any combination thereof. Accordingly, various methods can be utilized to prepare the supported transition metal catalyst particles, including, for example, extrusion, spray drying, pelletizing, marumerizing, spherodizing, agglomeration, oil drop, and the like, as well as combinations thereof.

In some aspects, the supported transition metal catalyst and the reduced transition metal catalyst have a relatively small particle size, in which representative ranges for the average (d50) particle size of the supported transition metal catalyst and the reduced transition metal catalyst can include from 10 to 500 microns, from 25 to 250 microns, from 20 to 100 microns, from 40 to 160 microns, or from 40 to 120 microns.

In other aspects, the supported transition metal catalyst and the reduced transition metal catalyst can be in the form of pellets or beads—and the like—having an average size ranging from 1/16 inch to 1/2 inch, or from 1/8 inch to 1/4 inch. As noted above, the size of the supported transition metal catalyst and/or reduced transition metal catalyst particles can be varied to suit the particular process for converting the hydrocarbon reactant into the alcohol compound and/or carbonyl compound.

A supported transition metal catalyst consistent with aspects of this invention can comprise a silica-coated alumina and from 0.01 to 50 wt. % of a transition metal comprising molybdenum, tungsten, vanadium, or a combination thereof, based on the weight of the catalyst. Accordingly, the transition metal can comprise molybdenum; alternatively, tungsten; or alternatively, vanadium.

The silica-coated alumina can have any suitable weight ratio of alumina to silica. While not limited thereto, the weight ratio can range from 1:20 to 20:1, such as from 1:5 to 5:1, from 3:1 to 1:3, from 1:1 to 3:1, from 1:1 to 2:1, or from 1.2:1 to 1.8:1. While the supported transition metal catalyst can contain from 0.01 to 50 wt. % of the transition metal, more often, the supported transition metal catalyst contains from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. %, of the transition metal, based on the weight of the supported transition metal catalyst.

Another supported transition metal catalyst consistent with aspects of this invention can comprise a solid support and from 0.01 to 50 wt. % of a transition metal comprising molybdenum, tungsten, vanadium, or a combination thereof, based on the weight of the catalyst. Further, at least one bonding site on the transition metal has a ligand characterized by one of the following formulas: —O-Hydrocarbon group or —O-Halogenated hydrocarbon group. The solid support for this supported transition metal catalyst can be any solid support disclosed herein, for instance, any solid oxide, any chemically-treated solid oxide, or any zeolite disclosed herein.

As above, while the supported transition metal catalyst can contain from 0.01 to 50 wt. % of the transition metal, more often, the supported transition metal catalyst contains from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. %, of the transition metal, based on the weight of the supported transition metal catalyst.

While not limited thereto, the molar ratio of the hydrocarbon group to transition metal generally can range from 0.25:1 to 2:1 in one aspect, from 0.5:1 to 2:1 in another aspect, from 0.5:1 to 1.5:1 in another aspect, from 0.75:1 to 1.75:1 in yet another aspect, and from 0.75:1 to 1.25:1 in still another aspect.

EXAMPLES 1-23

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Catalysts A1-A3 were prepared by dissolving ammonium metatungstate in water and depositing into a silica support (BET of 500 m$^2$/g, pore volume of 1.6 mL/g). After drying, the transition metal loading was 0.9-2.5 mmol W/g silica. The catalysts were calcined in dry air at 500° C. (A1), 650° C. (A2), or 700° C. (A3) for 3 hr prior to use.

Catalyst B1 was prepared by dissolving ammonium molybdenate in water and depositing into a silica support (BET of 500 m$^2$/g, pore volume of 1.6 mL/g). After drying, the transition metal loading was 2.0 mmol Mo/g silica. The catalyst was calcined in dry air at 600° C. for 3 hr prior to use. Catalyst B2 was impregnated with an aqueous solution of the same molybdenum compound to equal 1.0 mmol Mo/g silica. Then, it was dried and calcined in dry air at 700° C. for 3 hr.

Catalyst C was prepared by dissolving titanium isopropoxide in water containing 2 moles of oxalic acid per mole of titanium, and 3 moles of dimethylformamide per mole of titanium. The solution was then deposited onto a silica support (BET of 500 m$^2$/g, pore volume of 1.6 mL/g). After drying, the transition metal loading was 1.02 mmol Ti/g silica. The catalyst was calcined in dry air at 650° C. for 3 hr prior to use.

Catalyst D1 was prepared by dry mixing vanadium(IV) acetylacetonate, (VO(AcAc)$_2$) with silica (BET of 500 m$^2$/g, pore volume of 1.6 mL/g) to equal 2.0 mmol V/g silica. The dry mixture was calcined in dry air at 500° C. for 3 hr prior to use. Catalyst D2 was impregnated with a methanol solution of the same vanadium compound to equal 1.26 mmol V/g silica. Then, it was dried and calcined in dry air at 500° C. for 3 hr. Catalyst D3 was impregnated with a methanol solution of the same vanadium compound to equal 1.0 mmol V/g silica. Then, it was dried and calcined in dry air at 700° C. for 3 hr.

Catalyst E was prepared similarly to D2 except that the support was silica-coated alumina (BET of 450 m$^2$/g, pore volume of 1.4 mL/g, 40 wt. % silica) to equal 1.26 mmol V/g silica-coated alumina. The dry mixture was calcined in dry air at 500° C. for 3 hr prior to use.

BET surface areas can be determined using the BET nitrogen adsorption method of Brunauer et al., *J. Am. Chem. Soc.*, 60, 309 (1938) as described in ASTM D1993-91. Total pore volumes can be determined in accordance with Halsey, G. D., *J. Chem. Phys.* (1948), 16, pp. 931. The d50 particle size, or median or average particle size, refers to the particle size for which 50% of the sample by volume has a smaller size and 50% of the sample has a larger size, and can be determined using laser diffraction in accordance with ISO 13320.

Table I summarizes the reactions of Examples 1-14, in which the supported transition metal catalyst was first charged to an air-tight glass 100-mL glass container at 25° C., followed by the addition of the hydrocarbon reactant. The glass container was then exposed to a light source as noted in Table I. For all examples where the glass container was exposed to light, the container was slowly rotated at 5-10 rpm to turn over the catalyst particles in the bottle to ensure even exposure of the mixture of the supported transition metal catalyst and the hydrocarbon reactant to each other and to the light. For examples where the glass container was exposed to artificial light, the sample was placed in a box containing a fluorescent light or a LED light, where three 15 watt bulbs were placed in a plane about 3 inches apart and about 2 inches from the bottle. Reduction of the supported transition metal catalysts was monitored by the presence of a color change. The light sources used in Table I were blue fluorescent (425-475 nm) or blue LED (400-450 nm) at a lux of ~54,000-73,000, and UV LED (380-405 nm) at a lux of ~75,000-80,000.

After the desired exposure time, the reduced transition metal catalyst was mixed with a hydrolysis agent to cleave the hydrocarbon-containing ligand(s) from the reduced transition metal catalyst. The mixture was stirred for several minutes. The hydrolysis agent used was generally selected so as to not interfere with analysis of the reaction product (e.g., methanol was not used as the hydrolysis agent when the reaction product after hydrolysis could contain methanol, etc.).

Table I summarizes the results of Examples 1-14, and lists the specific supported transition metal catalyst and amount, the hydrocarbon reactant and amount, the light treatment and resulting color, the hydrolysis agent and amount, the acid/metal (molar), alcohol/metal (molar), the GC-MS/metal (molar), the total/metal (molar), and an analysis of the reaction product (oxygenated products) after hydrolysis. The reaction product analysis includes only oxygen-containing products that were derivable from the reductant/reactant and does not include, for example, materials resulting from the hydrolysis agent or its by-products, or oligomers resulting from polymerization. For the oxygenated reaction products, area % from the analytical procedures listed below is roughly equivalent to mol %, thus the results in Table I are shown in mol %.

Carboxylic acid products (and acid/metal ratios on a molar basis) were determined by first neutralizing the product acids with a solution of sodium hydroxide to put them into the ionic form. Then, a small amount of the sample was injected through an ion column designed to separate anions from weak organic acids through an ion chromatography process. A Dionex IC-3000 instrument with an ICE-AS1 column and guard was used. The test was specifically sensitive to linear carboxylic acids from $C_1$ to $C_6$, glutarate and glycolate ions. Results were reported in micrograms of carboxylate per mL of solution, which was then converted to moles.

Lower alcohol products (and alcohol/metal on a molar basis) were determined using a GC-MS procedure, with an Agilent 6890 gas chromatograph having a flame-ionizing detector (FID). It used a Restek Stapilwax column (P/N 10658) designed and gated specifically to separate and detect light alcohols. The procedure was gated for acetone, methanol, ethanol, isopropanol, n-propanol, isobutanol, n-butanol, t-butanol, 2-butanol, 2-butoxyethanol, acetonitrile and tetrahydrofuran.

Additional reaction products (and GC-MS/metal on a molar basis) were determined using another GC-MS procedure, as follows. Gas chromatography was performed using an Agilent 7890B GC equipped with both flame ionizing and mass spectral analysis. An all-purpose capillary column (Agilent J&W VF-5 ms, 30 m×0.25 mm×0.25 μm) was used with variable temperature. Approximately 0.5 μL sample aliquots were injected into a GC port held at 250° C. using a split ratio of 10:1. The carrier gas was ultra-high purity helium and was electronically controlled throughout the run to a constant flow rate of 1.2 mL/min. Initial column temperature was held at 50° C. for 5 min, ramped at 20° C./min to 250° C., and then held at 250° C. for 19 min. Spectral assignment was made via mass correlation using an Agilent 5977B mass spectrometer connected to the GC unit using electron ionization at 70 eV. The nominal mass range scanned was 14-400 m/z using a scan time of 0.5 sec. Nominal detector voltage used was 1200 V. For calibration purposes both the FID and MS detectors were sometimes used in sequence on the same or reference samples.

Due to the wide range of oxygenated products produced herein, one or all of these three procedures were used to characterize the reaction product after hydrolysis. In some cases, the same compound was detected by more than one technique, and this was subtracted out of the total/metal (on a molar basis) to prevent double counting of the same compound by more than one analytical technique. For the most part, however, there was very little overlap between the three analytical procedures.

Referring now to the data in Table I, while none of the catalysts in Examples 1-14 exhibit any (ethylene) polymerization activity whatsoever, alcohol and/or carbonyl (e.g., aldehyde, carboxylic acid) products were unexpectedly produced in these examples, with the exception of Examples 1 and 8-9. Surprisingly, the tungsten catalyst of Example 2 converted i-pentane (an alkane) into a reaction product containing 96% acetic acid, while the tungsten catalyst of Examples 4-6 converted methane (an alkane) into a reaction product that was either predominantly methanol or predominantly formic acid. Using olefin reactants, the tungsten catalyst of Example 3 converted 1-hexene into a reaction product containing 98% acetic acid, while the tungsten catalyst of Example 7 converted ethylene into a reaction product containing 90% methanol.

Example 9 used a titanium catalyst. Although titanium is known to be light sensitive using a different mechanism, no alcohol or carbonyl products were produced using this procedure.

The vanadium catalysts of Examples 10-11 and 14 converted n-pentane (an alkane) into a reaction product containing 90-100% pentanols. Using olefin reactants, the vanadium catalyst of Example 12 converted 1-hexene into a reaction product containing a wide range of oxygenated products including various hexanols, while the vanadium catalyst of Example 13 converted ethylene into a reaction product containing mostly lower alcohols, predominantly ethanol and methanol.

Table II summarizes the reactions of Examples 15-23, which were performed similarly to Examples 1-14. However, in Examples 15-23, an oxidizing atmosphere was provided by adding dry air (1 atm) to the 100-mL glass container, either "during" the reduction (while the catalyst and the hydrocarbon reactant were being contacted and irradiated) or at the "end" of the reduction (after irradiating, but before hydrolysis). This was accomplished by injecting a stream of dry air into the container over about 30 seconds, which usually resulted in an immediate color change. Total exposure time to the air, prior to hydrolysis, was approximately 1 minute. The light source used in Examples 15-17 in Table II was a UV LED (380-405 nm) at a lux of 75,000-80,000. For Examples 18-23, two ZMHA 60-watt LED ultraviolet lamps were used as the light source (380-420 nm), and the output was approximately 250,000 lux (the catalyst samples were placed 2 inches from the lamps).

Referring now to the data in Table II, Examples 15-23 demonstrate the conversion of alkanes (n-pentane) and olefins (ethylene and 1-hexene) into analogous alcohol and carbonyl products at ambient temperature using vanadium, tungsten, or molybdenum catalysts under a variety of irradiation treatments, oxygen exposures, and hydrolysis agents. Generally, as compared to Table I, the use of oxygen either during the reduction or at the end of the reduction (but prior to hydrolysis) resulted in an unexpected increase in the yield of the oxygenated products, as quantified by GC-MS products per transition metal on a molar basis. In some examples, the molar amount of redox products/metal was over 2, such as from 2.2 to 3.3. Of the vanadium, tungsten, or molybdenum supported catalysts, the vanadium catalysts generally produced the largest amount of alcohol/carbonyl products on a molar basis.

TABLE I

Summary of Examples 1-14

| Example | 1 | 2 | | 3 | | 4 | |
|---|---|---|---|---|---|---|---|
| Catalyst | 2.5 mmol W-A1 | 0.9 mmol W-A2 | | 0.9 mmol W-A2 | | 0.9 mmol W-A2 | |
| Weight (g) | 6.3 | 2.0 | | 2.2 | | 4.0 | |
| Reductant | n-Pentane | i-Pentane | | 1-Hexene | | Methane | |
| Amount | 0.5 mL | 0.5 mL | | 0.5 mL | | 15 psig | |
| Light | 3 hr Blue | 44 hr Blue | | 44 hr Blue | | 24 hr UV | |
| Color | Blue-green | Blue-green | | Dark blue-green | | Yellow-green | |
| Hydrolysis | 10% $H_2O$/MeOH | $H_2O$ + $CH_3CN$ | | $H_2O$ + $CH_3CN$ | | $H_2O$ | |
| Amount (mL) | 11 | 15 | | 15 | | 15 | |
| Acid/metal | 0.000 | 0.042 | | 0.041 | | 0.001 | |
| Alcohol/metal | na | 0.000 | | 0.000 | | 0.008 | |
| GC-MS/metal | 0.000 | 0.021 | | 0.020 | | 0.000 | |
| Total/metal | 0.000 | 0.044 | | 0.042 | | 0.008 | |
| Oxygenated Products | No Products Detected | acetic acid isobutanoic acid $C5H10O2$ | 96% 2% 2% | acetic acid 2-hexanol | 98% 2% | methanol formic acid | 94% 6% |

| Example | 5 | | 6 | | 7 | | 8 | |
|---|---|---|---|---|---|---|---|---|
| Catalyst | 0.9 mmol W-A2 | | 0.9 mmol W-A2 | | 0.9 mmol W-A2 | | 2 mmol Mo-B1 | |
| Weight (g) | 2.1 | | 2.1 | | 2.0 | | 0.1 | |
| Reductant | Methane | | Methane | | Ethylene | | n-Pentane | |
| Amount | 15 psig | | 15 psig | | 15 psig | | 0.6 mL | |
| Light | 24 hr UV | | 44 hr Blue | | 44 hr Blue | | 2.4 hr Blue | |
| Color | Yellow-green | | Yellow-green | | Blue | | Light blue-metallic green | |
| Hydrolysis | $H_2O$ | | $H_2O$ + $CH_3CN$ | | $H_2O$ + $CH_3CN$ | | 10% $H_2O$/MeOH | |
| Amount (mL) | 15 | | 15 | | 15 | | 12 | |
| Acid/metal | 0.002 | | 0.001 | | 0.001 | | 0.000 | |
| Alcohol/metal | 0.023 | | 0.000 | | 0.009 | | na | |
| GC-MS/metal | 0.000 | | 0.000 | | 0.000 | | 0.000 | |
| Total/metal | 0.025 | | 0.001 | | 0.010 | | 0.000 | |
| Oxygenated Products | methanol formic acid | 93% 7% | formic acid | 100% | methanol isopropanol formic acid acetic acid | 90% 6% 3% <1% | No Products Detected | |

| Example | 9 | | 10 | | 11 | | 12 | |
|---|---|---|---|---|---|---|---|---|
| Catalyst | 1 mmol Ti-C | | 2 mmol V-D1 | | 1.26 mmol V-D2 | | 1.26 mmol V-D2 | |
| Weight (g) | 3.9 | | 1.5 | | 2.0 | | 2.1 | |
| Reductant | n-Pentane | | n-Pentane | | n-Pentane | | 1-Hexene | |
| Amount | 2 mL | | 1 mL | | 2 mL | | 2 mL | |
| Light | 26 hr UV | | 8 hr UV | | UV 24 h | | UV 24 h | |
| Color | White | | Red-brown | | Pale yellow | | Pale yellow | |
| Hydrolysis | 5% $H_2O$/MeOH | | 10% $H_2O$/MeOH | | 5% $H_2O$/MeOH | | 5% $H_2O$/MeOH | |
| Amount (mL) | 10 | | 12 | | 15 | | 15 | |
| Acid/metal | 0.000 | | 0.000 | | 0.0003 | | 0.0003 | |
| Alcohol/metal | 0.000 | | na | | 0.007 | | 0.023 | |
| GC-MS/metal | 0.000 | | 0.496 | | 2.016 | | 1.610 | |
| Total/metal | 0.000 | | 0.496 | | 2.023 | | 1.633 | |
| Oxygenated Products | No Products Detected | | 1-pentanol 2-pentanol 3-pentanol | 50% 40% 10% | 2-pentanol 1-pentanol $C5H10O2$ isopropanol | 64% 32% 4% <1% | C18 oxygenate 2-hexanol 3-hexanol C9-10 oxygenate | 50% 27% 5% 4% |

TABLE I-continued

|  |  |  |  |  |  |
|---|---|---|---|---|---|
|  | ethanol | <1% | C6H14O | 3% |  |
|  |  |  | 2-hexanone | 1% |  |
|  |  |  | C10-14 oxygenate | 1% |  |
|  |  |  | 5-hexen-2-ol | 1% |  |
|  |  |  | 5-hexen-1-ol | 1% |  |

| Example | | 13 | 14 |
|---|---|---|---|
| Catalyst | | 1.26 mmol V-D2 | 1.26 mmol V-E |
| Weight (g) | | 1.8 | 2.0 |
| Reductant | | Ethylene | n-Pentane |
| Amount | | 2 atm | 2 mL |
| Light | | UV 24 h | UV 24 h |
| Color | | Pale yellow | Pale yellow |
| Hydrolysis | | 5% H$_2$O/MeOH | 5% H$_2$O/MeOH |
| Amount (mL) | | 15 | 15 |
| Acid/metal | | 0.0003 | |
| Alcohol/metal | | 0.065 | |
| GC-MS/metal | | 0.003 | 0.033 |
| Total/metal | | 0.068 | 0.033 |
| Oxygenated Products | ethanol | 52% | 2-pentanol 53% |
|  | methanol | 19% | 1-pentanol 36% |
|  | C6H14O | 8% | 3-pentanol 11% |
|  | 2-butanol | 6% |  |
|  | n-propanol | 3% |  |
|  | C6H12O aldehyde | 2% |  |
|  | C5-8 dioxygenate | 2% |  |

TABLE II

Summary of Examples 15-23

| Example | 15 | 16 | 17 |
|---|---|---|---|
| Catalyst | 1.26 mmol V-D2 | 1.26 mmol V-D2 | 1.26 mmol V-D2 |
| Weight (g) | 2.0 | 2.4 | 2.4 |
| Reductant | n-pentane | ethylene | 1-hexene |
| Amount | 2 mL | 1 atm | 2 mL |
| Air with reductant | 1 atm | 1 atm | 1 atm |
| Light | UV 24 h | UV 24 h | UV 24 h |
| Color | dark brown | brown | black |
| Air after reduction | none | none | none |
| Hydrolysis | 5% H$_2$O/MeOH | H$_2$O | 4% H$_2$O/MeOH |
| Amount (mL) | 15 | 15 | 15 |
| Acid/metal | Not analyzed | Not analyzed | Not analyzed |
| Alcohol/metal | Not analyzed | Not analyzed | Not analyzed |
| GC-MS/metal | 3.338 | 0.0317 | 2.249 |
| Total/metal | 3.338 | 0.0317 | 2.249 |
| Oxygenated Products | 2-pentanol 64% | ethanediol 55% | 2-hexanol 31% |
|  | 1-pentanol 18% | formic acid 35% | C6 oxygenate 8% |
|  | pentene 13% | C3H6O3 10% | C12 oxygenate 5% |
|  | pentanediol 2% |  | C12 oxygenate 4% |
|  | 3-penten-2-one 2% |  | C12 oxygenate 4% |
|  |  |  | C12 oxygenate 3% |
|  |  |  | C18 oxygenate 3% |
|  |  |  | C12 oxygenate 3% |
|  |  |  | C12 oxygenate 3% |

| Example | 18 | 19 | 20 |
|---|---|---|---|
| Catalyst | 1.0 mmol W-A3 | 1.0 mmol W-A3 | 1.0 mmol V-D3 |
| Weight (g) | 2.8 | 3.3 | 1.9 |
| Reductant | n-pentane | n-pentane | n-pentane |
| Amount | 1 mL | 1 mL | 1 mL |
| Air with reductant | none | 1 atm | none |
| Light | UV 2 h | UV 17 h | UV 2 h |
| Color | blue-green | blue-green | black-brown |
| Air after reduction | 1 atm | none | 1 atm |
| Hydrolysis | 10% H$_2$O/EtOH | 10% H$_2$O/EtOH | 10% H$_2$O/EtOH |
| Amount (mL) | 15 | 15 | 15 |
| Acid/metal | Not analyzed | Not analyzed | Not analyzed |

TABLE II-continued

| | | | | | |
|---|---|---|---|---|---|
| Alcohol/metal | Not analyzed | | Not analyzed | | Not analyzed |
| GC-MS/metal | 0.002 | | 0.024 | | 0.093 |
| Total/metal | 0.002 | | 0.024 | | 0.093 |
| Oxygenated Products | pentene 100% | | 2-pentanol 69% | | 2-pentanol 71% |
| | | | 2-pentanone 14% | | 1-pentanol 9% |
| | | | 3-pentanone 7% | | pentanediol 7% |
| | | | pentanediol 6% | | 1,1-diethoxypentane 5% |
| | | | pentene 4% | | 2-pentanone 3% |
| | | | | | pentene 2% |
| | | | | | 3-pentanone 2% |

| Example | 21 | 22 | 23 |
|---|---|---|---|
| Catalyst | 1.0 mmol V-D3 | 1.0 mmol Mo-B2 | 1.0 mmol Mo-B2 |
| Weight (g) | 2.0 | 2.9 | 3.1 |
| Reductant | n-pentane | n-pentane | n-pentane |
| Amount | 1 mL | 1 mL | 1 mL |
| Air with reductant | 1 atm | none | 1 atm |
| Light | UV 17 h | UV 2 h | UV 17 h |
| Color | black-brown | gray | blue-green |
| Air after reduction | none | 1 atm | none |
| Hydrolysis | 10% $H_2O$/EtOH | 10% $H_2O$/EtOH | 10% $H_2O$/EtOH |
| Amount (mL) | 15 | 15 | 15 |
| Acid/metal | Not analyzed | Not analyzed | Not analyzed |
| Alcohol/metal | Not analyzed | Not analyzed | Not analyzed |
| GC-MS/metal | 0.148 | 0.003 | 0.013 |
| Total/metal | 0.148 | 0.003 | 0.013 |
| Oxygenated Products | 2-pentanol 59% | pentene 55% | pentanediol 44% |
| | 1-pentanol 18% | 2-pentanol 45% | 2-pentanol 20% |
| | pentanediol 11% | | 2-pentenal 10% |
| | 1,1-diethoxypentane 4% | | 1-pentanol 10% |
| | 2-pentanone 3% | | 2-pentanone 8% |
| | 3-pentanone 2% | | 3-pentanone 8% |
| | pentene 2% | | |
| | C10H22O2 2% | | |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for converting a hydrocarbon reactant into an alcohol compound and/or a carbonyl compound, the process comprising:

(i) irradiating the hydrocarbon reactant and a supported transition metal catalyst comprising molybdenum, tungsten, vanadium, or a combination thereof, with a light beam at a wavelength in the UV-visible spectrum to reduce at least a portion of the supported transition metal catalyst to form a reduced transition metal catalyst; and (ii) hydrolyzing the reduced transition metal catalyst to form a reaction product comprising the alcohol compound and/or the carbonyl compound.

Aspect 2. The process defined in aspect 1, wherein step (i) comprises irradiating the hydrocarbon reactant and the supported transition metal catalyst in an oxidizing atmosphere.

Aspect 3. A process for converting a hydrocarbon reactant into an alcohol compound and/or a carbonyl compound, the process comprising:

(I) irradiating the hydrocarbon reactant and a supported transition metal catalyst comprising molybdenum, tungsten, vanadium, or a combination thereof, with a light beam at a wavelength in the UV-visible spectrum to reduce at least a portion of the supported transition metal catalyst to form a reduced transition metal catalyst;

(II) subjecting the reduced transition metal catalyst to an oxidizing atmosphere; and (III) hydrolyzing the reduced transition metal catalyst to form a reaction product comprising the alcohol compound and/or the carbonyl compound.

Aspect 4. The process defined in any one of aspects 1-3, wherein the hydrocarbon reactant comprises a saturated or an unsaturated, linear or branched or cyclic, aliphatic hydrocarbon, and including combinations thereof.

Aspect 5. The process defined in any one of aspects 1-3, wherein the hydrocarbon reactant comprises a linear alkane compound, a branched alkane compound, a cyclic alkane compound, or a combination thereof.

Aspect 6. The process defined in any one of aspects 1-3, wherein the hydrocarbon reactant comprises any suitable carbon number alkane compound or any carbon number alkane compound disclosed herein, e.g., a $C_1$ to $C_{36}$ alkane compound, a $C_1$ to $C_{18}$ alkane compound, a $C_1$ to $C_{12}$ alkane compound, or a $C_1$ to $C_8$ alkane compound.

Aspect 7. The process defined in any one of aspects 1-3, wherein the hydrocarbon reactant comprises methane, ethane, propane, butane (e.g., n-butane or isobutane), pentane (e.g., n-pentane, neopentane, cyclopentane, or isopentane), hexane, heptane, octane, nonane, decane, undecane, dodecane, tridecane, tetradecane, pentadecane, hexadecane, heptadecane, octadecane, or any combination thereof.

Aspect 8. The process defined in any one of aspects 1-3, wherein the hydrocarbon reactant comprises methane, ethane, propane, n-butane, isobutane, n-pentane, neopentane, isopentane, n-hexane, n-heptane, n-octane, n-decane, n-dodecane, or any combination thereof or the hydrocarbon reactant comprises methane, ethane, propane, butane, pentane, hexane, or any combination thereof.

Aspect 9. The process defined in any one of aspects 1-3, wherein the hydrocarbon reactant comprises a linear olefin compound (e.g., an α-olefin), a branched olefin compound, a cyclic olefin compound, or a combination thereof.

Aspect 10. The process defined in any one of aspects 1-3, wherein the hydrocarbon reactant comprises any suitable carbon number olefin compound or any carbon number olefin compound disclosed herein, e.g., a $C_2$ to $C_{36}$ olefin compound, a $C_2$ to $C_{18}$ olefin compound, a $C_2$ to $C_{12}$ olefin compound, or a $C_2$ to $C_8$ olefin compound.

Aspect 11. The process defined in any one of aspects 1-3, wherein the hydrocarbon reactant comprises ethylene, propylene, 1-butene, 1-pentene, 2-pentene, 1-hexene, 1-heptene, 1-octene, 1-decene, 1-dodecene, 1-tetradecene, 1-hexadecene, 1-octadecene, cyclopentene, cyclohexene, or any combination thereof.

Aspect 12. The process defined in any one of aspects 1-3, wherein the hydrocarbon reactant comprises an aromatic compound (e.g., benzene, toluene, xylene, styrene, and substituted versions thereof, and including combinations thereof).

Aspect 13. The process defined in any one of aspects 1-3, wherein the hydrocarbon reactant comprises any suitable carbon number aromatic compound or any carbon number aromatic compound disclosed herein, e.g., a $C_6$ to $C_{36}$ aromatic compound, a $C_6$ to $C_{18}$ aromatic compound, a $C_6$ to $C_{12}$ aromatic compound, or a $C_6$ to $C_8$ aromatic compound.

Aspect 14. The process defined in any one of aspects 1-3, wherein the hydrocarbon reactant comprises benzene, toluene, ethylbenzene, xylene, styrene, mesitylene, or any combination thereof.

Aspect 15. The process defined in any one of aspects 1-3, wherein the hydrocarbon reactant comprises a $C_n$ hydrocarbon compound, the alcohol compound comprises a $C_n$ alcohol compound, and the carbonyl compound comprises a $C_n$ carbonyl compound.

Aspect 16. The process defined in aspect 15, wherein n is any suitable integer or an integer in any range disclosed herein, e.g., from 1 to 36, from 1 to 18, from 1 to 12, or from 1 to 8.

Aspect 17. The process defined in any one of aspects 1-3, wherein the hydrocarbon reactant comprises a $C_n$ hydrocarbon compound, the alcohol compound comprises a $(C_{n+1})+$ alcohol compound, and/or the carbonyl compound comprises a $(C_{n+1})+$ carbonyl compound.

Aspect 18. The process defined in aspect 17, wherein n is any suitable integer or an integer in any range disclosed herein, e.g., from 1 to 36, from 1 to 18, from 1 to 12, or from 1 to 8.

Aspect 19. The process defined in any one of aspects 1-3, wherein the hydrocarbon reactant comprises a $C_n$ hydrocarbon compound, the alcohol compound comprises a $(C_{n-1})-$ alcohol compound, and/or the carbonyl compound comprises a $(C_{n-1})-$ carbonyl compound.

Aspect 20. The process defined in aspect 19, wherein n is any suitable integer or an integer in any range disclosed herein, e.g., from 2 to 36, from 2 to 18, from 2 to 12, or from 2 to 8.

Aspect 21. The process defined in any one of the preceding aspects, wherein the supported transition metal catalyst comprises molybdenum; alternatively, tungsten; or alternatively, vanadium.

Aspect 22. The process defined in any one of the preceding aspects, wherein the supported transition metal catalyst and the reduced transition metal catalyst comprise any suitable amount of transition metal or an amount in any range disclosed herein, e.g., from 0.01 to 50 wt. %, from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. % of transition metal, based on the weight of the supported transition metal catalyst or the reduced transition metal catalyst.

Aspect 23. The process defined in any one of the preceding aspects, wherein at least 10 wt. %, at least 20 wt. %, at least 40 wt. %, at least 60 wt. %, at least 80 wt. %, or at least 90 wt. %, of the supported transition metal catalyst is reduced to form the reduced transition metal catalyst in step (i) or step (I), based on the total amount of the supported transition metal catalyst.

Aspect 24. The process defined in any one of aspects 1-23, wherein the supported transition metal catalyst and the reduced transition metal catalyst comprise any suitable solid oxide or any solid oxide disclosed herein, e.g., silica, alumina, silica-alumina, silica-coated alumina, aluminum phosphate, aluminophosphate, heteropolytungstate, titania, zirconia, magnesia, boria, zinc oxide, silica-titania, silica-zirconia, alumina-titania, alumina-zirconia, zinc-aluminate, alumina-boria, alumina borate, silica-boria, aluminophosphate-silica, titania-zirconia, or any combination thereof.

Aspect 25. The process defined in any one of aspects 1-23, wherein the supported transition metal catalyst and the reduced transition metal catalyst comprise silica, silica-alumina, silica-coated alumina, silica-titania, silica-titania-magnesia, silica-zirconia, silica-magnesia, silica-boria, aluminophosphate-silica, alumina, alumina borate, or any combination thereof.

Aspect 26. The process defined in any one of aspects 1-23, wherein the supported transition metal catalyst and the reduced transition metal catalyst comprise a chemically-treated solid oxide comprising a solid oxide (e.g., as in aspect 24 or 25, such as silica, alumina, silica-alumina, silica-titania, silica-zirconia, silica-yttria, aluminophosphate, zirconia, titania, thoria, or stania) treated with an electron-withdrawing anion.

Aspect 27. The process defined in aspect 26, wherein the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, molybdate, or any combination thereof.

Aspect 28. The process defined in aspect 26 or 27, wherein the chemically-treated solid oxide contains from 1 to 30 wt. %, from 2 to 20 wt. %, from 2 to 15 wt. %, from 3 to 12 wt. %, or from 4 to 10 wt. %, of the electron-withdrawing anion, based on the total weight of the chemically-treated solid oxide.

Aspect 29. The process defined in any one of aspects 1-23, wherein the supported transition metal catalyst and the reduced transition metal catalyst comprise a chemically-treated solid oxide comprising fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Aspect 30. The process defined in any one of aspects 1-23, wherein the supported transition metal catalyst and the reduced transition metal catalyst comprise a zeolite.

Aspect 31. The process defined in aspect 30, wherein the supported transition metal catalyst and the reduced transition metal catalyst comprise a medium pore zeolite, a large pore zeolite, or a combination thereof.

Aspect 32. The process defined in aspect 30, wherein the zeolite comprises a ZSM-5 zeolite, a ZSM-11 zeolite, an EU-1 zeolite, a ZSM-23 zeolite, a ZSM-57 zeolite, an ALPO4-11 zeolite, an ALPO4-41 zeolite, a Ferrierite framework type zeolite, or a combination thereof.

Aspect 33. The process defined in aspect 30, wherein the supported transition metal catalyst and the reduced transition metal catalyst comprise an L-zeolite, a Y-zeolite, a mordenite, an omega zeolite, and/or a beta zeolite.

Aspect 34. The process defined in any one of aspects 30-33, wherein the supported transition metal catalyst and the reduced transition metal catalyst comprise the zeolite and any suitable amount of binder or an amount in any range disclosed herein, e.g., from 3 wt. % to 35 wt. %, or from 5 wt. % to 30 wt. % binder, based on the weight of the supported transition metal catalyst and/or the reduced transition metal catalyst.

Aspect 35. The process defined in any one of the preceding aspects, wherein the supported transition metal catalyst and the reduced transition metal catalyst have any suitable pore volume (total) or a pore volume (total) in any range disclosed herein, e.g., from 0.1 to 5 mL/g, from 0.15 to 5 mL/g, from 0.1 to 3 mL/g, from 0.15 to 2 mL/g, from 0.3 to 1.5 mL/g, or from 0.5 to 1.0 mL/g.

Aspect 36. The process defined in any one of the preceding aspects, wherein the supported transition metal catalyst and the reduced transition metal catalyst have any suitable BET surface area or a BET surface area in any range disclosed herein, e.g., from 50 to 2000 $m^2/g$, from 50 to 700 $m^2/g$, from 50 to 400 $m^2/g$, from 100 to 1200 $m^2/g$, or from 150 to 525 $m^2/g$.

Aspect 37. The process defined in any one of the preceding aspects, wherein the supported transition metal catalyst and the reduced transition metal catalyst are in any suitable shape or form or any shape or form disclosed herein, e.g., powder, round or spherical (e.g., spheres), ellipsoidal, pellet, bead, cylinder, granule (e.g., regular and/or irregular), trilobe, quadralobe, ring, wagonwheel, monolith, or any combination thereof.

Aspect 38. The process defined in any one aspects 1-37, wherein the supported transition metal catalyst and the reduced transition metal catalyst have any suitable average (d50) particle size or an average (d50) particle size in any range disclosed herein, e.g., from 10 to 500 microns, from 25 to 250 microns, or from 20 to 100 microns.

Aspect 39. The process defined in any one aspects 1-37, wherein the supported transition metal catalyst and the reduced transition metal catalyst comprise pellets or beads having any suitable average size or an average size in any range disclosed herein, e.g., from 1/16 inch to 1/2 inch, or from 1/8 inch to 1/4 inch.

Aspect 40. The process defined in any one of aspects 1-39, wherein the wavelength comprises a single wavelength or a range of wavelengths in the visible spectrum (from 380 nm to 780 nm).

Aspect 41. The process defined in any one of aspects 1-39, wherein the wavelength comprises a single wavelength or a range of wavelengths in the 200 nm to 750 nm range.

Aspect 42. The process defined in any one of aspects 1-39, wherein the wavelength comprises a single wavelength or a range of wavelengths in the 300 to 750 nm range, the 350 nm to 650 nm range, the 300 nm to 500 nm range, or the 300 nm to 400 nm range.

Aspect 43. The process defined in any one of aspects 1-39, wherein the wavelength comprises a single wavelength or a range of wavelengths below 600 nm, below 500 nm, below 475 nm, below 450 nm, below 430 nm, or below 420 nm.

Aspect 44. The process defined in any one of aspects 1-43, wherein the wavelength is a single wavelength.

Aspect 45. The process defined in any one of aspects 1-43, wherein the wavelength is a range of wavelengths spanning at least 25 nm, at least 50 nm, at least 100 nm, or at least 200 nm.

Aspect 46. The process defined in any one of the preceding aspects, wherein the light beam has any suitable intensity or an intensity in any range disclosed herein, e.g., at least 500 lumens, at least 1000 lumens, at least 2000 lumens, at least 5000 lumens, at least 10,000 lumens, or at least 20,000 lumens.

Aspect 47. The process defined in any one of the preceding aspects, wherein the light beam is from a light source having any suitable power or any power disclosed herein, e.g., at least 50 watts, at least 100 watts, at least 200 watts, at least 500 watts, at least 1,000 watts, or at least 2,000 watts.

Aspect 48. The process defined in any one of the preceding aspects, wherein the hydrocarbon reactant and the supported transition metal catalyst are irradiated with any suitable illuminance or any illuminance disclosed herein, e.g., at least 100 lux, at least 500 lux, at least 1000 lux, at least 2000 lux, at least 5000 lux, at least 10,000 lux, at least 20,000 lux, at least 50,000 lux, or at least 100,000 lux.

Aspect 49. The process defined in any one of the preceding aspects, wherein the irradiating step (or subjecting step) is conducted at any suitable temperature or any temperature disclosed herein, e.g., less than 200° C., less than 100° C., less than 40° C., from −100° C. to 100° C., from 0° C. to 100° C., or from 10° C. to 40° C.

Aspect 50. The process defined in any one of the preceding aspects, wherein the irradiating step (or subjecting step) is conducted for any suitable exposure time or for any exposure time disclosed herein, e.g., from 15 sec to 48 hr, from 1 min to 6 hr, from 1 min to 15 min, or from 1 hr to 8 hr.

Aspect 51. The process defined in any one of the preceding aspects, wherein the molar ratio of the hydrocarbon reactant to transition metal (of the supported transition metal catalyst) is in any suitable range or any range disclosed herein, e.g., at least 0.25:1, at least 0.5:1, at least 1:1, at least 10:1, at least 100:1, at least 1000:1, or at least 10,000:1.

Aspect 52. The process defined in any one of aspects 1-51, wherein the hydrocarbon reactant is in a gas phase during the irradiating step.

Aspect 53. The process defined in any one of aspects 1-51, wherein the hydrocarbon reactant is in a liquid phase during the irradiating step.

Aspect 54. The process defined in any one of aspects 1-51, wherein the process comprises irradiating a slurry of the supported transition metal catalyst in the hydrocarbon reactant.

Aspect 55. The process defined in any one of aspects 1-51, wherein the process comprises contacting the hydrocarbon reactant with a fluidized bed of the supported transition metal catalyst, and irradiating while contacting (fluidizing).

Aspect 56. The process defined in any one of aspects 1-51, wherein the process comprises contacting the hydrocarbon reactant (e.g., in a gas phase or in a liquid phase) with a fixed bed of the supported transition metal catalyst, and irradiating while contacting.

Aspect 57. The process defined in any one of the preceding aspects, wherein the step of irradiating the hydrocarbon reactant with the supported transition metal catalyst is conducted at any suitable WHSV or a WHSV in any range disclosed herein, e.g., from 0.01 hr$^{-1}$ to 500 hr$^{-1}$, or from 0.1 hr$^{-1}$ to 10 hr$^{-1}$.

Aspect 58. The process defined in any one of the preceding aspects, wherein the hydrolyzing step is conducted at any suitable temperature or any temperature disclosed herein, e.g., less than 200° C., less than 100° C., less than 40° C., from 0° C. to 100° C., or from 10° C. to 40° C.

Aspect 59. The process defined in any one of the preceding aspects, wherein the hydrolyzing step comprises contacting the reduced transition metal catalyst with a hydrolysis agent.

Aspect 60. The process defined in aspect 59, wherein the hydrolysis agent comprises any suitable hydrolysis agent or any hydrolysis agent disclosed herein, e.g., water, steam, an alcohol agent, an acid agent, an alkaline agent, or any combination thereof.

Aspect 61. The process defined in aspect 59 or 60, wherein the hydrolysis agent further comprises any suitable reducing agent or any reducing agent disclosed herein, e.g., ascorbic acid, an iron (II) reducing agent, ferrous (II) ions, a zinc reducing agent, sodium bisulfite, sodium thiosulfate, sodium sulfide, or any combination thereof.

Aspect 62. The process defined in any one of the preceding aspects, wherein the carbonyl compound comprises an aldehyde compound, a ketone compound, an organic acid compound, or any combination thereof; additionally or alternatively, the alcohol compound comprises a diol, an allylic alcohol, a phenol, or any combination thereof.

Aspect 63. The process defined in any one of the preceding aspects, wherein a conversion of the hydrocarbon reactant (or a yield to the alcohol compound, or a yield to the carbonyl compound) is any percent conversion (or yield) disclosed herein, e.g., at least 2 wt. %, at least 5 wt. %, at least 10 wt. %, or at least 15 wt. % (and up to 99 wt. %, 95 wt. %, 90 wt. %, 80 wt. %, 70 wt. %, or 50 wt. %).

Aspect 64. The process defined in any one of the preceding aspects, wherein a single pass conversion of the hydrocarbon reactant (or a single pass yield to the alcohol compound, or a single pass yield to the carbonyl compound) is any single pass percent conversion (or single pass yield) disclosed herein, e.g., at least 2 wt. %, at least 5 wt. %, at least 10 wt. %, or at least 15 wt. % (and up to 99 wt. %, 95 wt. %, 90 wt. %, 80 wt. %, 70 wt. %, or 50 wt. %).

Aspect 65. The process defined in any one of the preceding aspects, wherein the yield to the alcohol compound (or the carbonyl compound) per mole of the transition metal in the supported transition metal catalyst is any molar ratio based on moles of the transition metal disclosed herein, e.g., at least 0.01, at least 0.05, at least 0.1, or at least 0.25 moles (and up to 10, up to 8, up to 5, up to 3, up to 2, up to 1.5, or up to 1 mole) of the alcohol compound (or the carbonyl compound).

Aspect 66. The process defined in any one of the preceding aspects, further comprising a step of separating at least a portion (and in some cases, all) of the hydrocarbon reactant from the reaction product after the hydrolyzing step to produce a separated hydrocarbon portion using any suitable technique or any technique disclosed herein, e.g., extraction, filtration, evaporation, distillation, or any combination thereof.

Aspect 67. The process defined in aspect 66, wherein the separated hydrocarbon portion is recycled and irradiated with the supported transition metal catalyst again.

Aspect 68. The process defined in any one of the preceding aspects, further comprising a step of separating at least a portion (and in some cases, all) of the alcohol compound and/or the carbonyl compound from the reaction product using any suitable technique or any technique disclosed herein, e.g., extraction, filtration, evaporation, distillation, or any combination thereof.

Aspect 69. The process defined in any one of the preceding aspects, further comprising a step of separating at least a portion (and in some cases, all) of the reduced transition metal catalyst from the reaction product after the hydrolyzing step to produce a separated reduced transition metal catalyst using any suitable technique or any technique disclosed herein, e.g., extraction, filtration, evaporation, distillation, or any combination thereof.

Aspect 70. The process defined in any one of the preceding aspects, further comprising a step of calcining the reduced transition metal catalyst or the separated reduced transition metal catalyst to regenerate the supported transition metal catalyst.

Aspect 71. The process defined in aspect 70, wherein calcining comprises subjecting the reduced transition metal catalyst or the separated reduced transition metal catalyst to an oxidizing atmosphere at any suitable peak temperature and time conditions or any peak temperature and time conditions disclosed herein, e.g., a peak temperature from 300° C. to 1000° C., from 500° C. to 900° C., or from 550° C. to 870° C., for a time period of from 1 min to 24 hr, from 1 hr to 12 hr, or from 30 min to 8 hr.

Aspect 72. The process defined in any one of aspects 2-71, wherein the oxidizing atmosphere comprises any suitable oxidizing atmosphere or any oxidizing atmosphere disclosed herein, e.g., oxygen, air, a mixture of air and an inert gas (such as nitrogen), a mixture of oxygen and an inert gas, NO, $NO_2$, $N_2O$, ozone, a halide oxide, $H_2O_2$, an organic peroxide, as well as combinations thereof.

Aspect 73. A supported transition metal catalyst comprising:

a silica-coated alumina; and from 0.01 to 50 wt. % of a transition metal comprising molybdenum, tungsten, vanadium, or a combination thereof, based on the weight of the catalyst.

Aspect 74. The catalyst defined in aspect 73, wherein the transition metal comprises molybdenum; alternatively, tungsten; or alternatively, vanadium.

Aspect 75. The catalyst defined in aspect 73 or 74, wherein the supported transition metal catalyst comprises any suitable amount of transition metal or an amount in any range disclosed herein, e.g., from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. % of transition metal, based on the weight of the supported transition metal catalyst.

Aspect 76. The catalyst defined in any one of aspects 73-75, wherein the silica-coated alumina has any suitable weight ratio of alumina to silica or a weight ratio in any range disclosed herein, e.g., from 1:20 to 20:1, from 1:5 to 5:1, from 3:1 to 1:3, from 1:1 to 3:1, from 1:1 to 2:1, or from 1.2:1 to 1.8:1.

Aspect 77. The catalyst defined in any one of aspects 73-76, wherein the supported transition metal catalyst comprises a the transition metal having an oxo bond, or comprises the transition metal in at least a +3 oxidation state, or comprises the transition metal in one of its uppermost two oxidation states, or any combination thereof.

Aspect 78. A supported transition metal catalyst comprising:
a solid support; and
from 0.01 to 50 wt. % of a transition metal comprising molybdenum, tungsten, vanadium, or a combination thereof, based on the weight of the catalyst; wherein:
at least one bonding site on the transition metal has a ligand characterized by one of the following formulas: —O-Hydrocarbon group or —O-Halogenated hydrocarbon group.

Aspect 79. The catalyst defined in aspect 78, wherein the molar ratio of the hydrocarbon group to transition metal is in any suitable range or any range disclosed herein, e.g., from 0.25:1 to 2:1, from 0.5:1 to 2:1, from 0.5:1 to 1.5:1, from 0.75:1 to 1.75:1, or from 0.75:1 to 1.25:1.

Aspect 80. The catalyst defined in aspect 78 or 79, wherein the supported transition metal catalyst comprises any suitable amount of the transition metal or an amount in any range disclosed herein, e.g., from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. % of transition metal, based on the weight of the supported transition metal catalyst.

Aspect 81. The catalyst defined in any one of aspects 78-80, wherein the solid support comprises any suitable solid support or any solid support disclosed herein, e.g., a solid oxide, a chemically-treated solid oxide, a zeolite, or any combination thereof.

We claim:

1. A process for converting a hydrocarbon reactant into an alcohol compound and/or a carbonyl compound, the process comprising:
   (i) irradiating the hydrocarbon reactant and a supported transition metal catalyst comprising molybdenum, tungsten, vanadium, or a combination thereof, with a light beam at a wavelength in the UV-visible spectrum to reduce at least a portion of the supported transition metal catalyst to form a reduced transition metal catalyst; and
   (ii) hydrolyzing the reduced transition metal catalyst to form a reaction product comprising the alcohol compound and/or the carbonyl compound.

2. The process of claim 1, wherein step (i) comprises irradiating the hydrocarbon reactant and the supported transition metal catalyst in an oxidizing atmosphere.

3. The process of claim 1, wherein the hydrocarbon reactant comprises a $C_1$ to $C_{36}$ linear, branched, or cyclic alkane compound.

4. The process of claim 1, wherein the hydrocarbon reactant comprises a $C_2$ to $C_{36}$ olefin compound, a $C_6$ to $C_{36}$ aromatic compound, or any combination thereof.

5. The process of claim 1, wherein the supported transition metal catalyst contains from 0.01 to 50 wt. % of molybdenum, tungsten, vanadium, or a combination thereof, based on the weight of the supported transition metal catalyst.

6. The process of claim 1, wherein:
the supported transition metal catalyst comprises a solid oxide, a chemically-treated solid oxide, a zeolite, or a combination thereof;
the supported transition metal catalyst has a pore volume from 0.1 to 5 mL/g and a BET surface area from 50 to 2000 m²/g; and
the irradiating step is conducted at a temperature from −100° C. to 100° C.

7. The process of claim 1, wherein;
the light beam is from a blue light source or a UV light source;
the light beam comprises wavelengths above 350 nm and below 500 nm;
the hydrocarbon reactant and the supported transition metal catalyst are irradiated with an illuminance of at least 5000 lux; or
any combination thereof.

8. The process of claim 1, wherein the process comprises:
contacting the hydrocarbon reactant with a fluidized bed of the supported transition metal catalyst, and irradiating while contacting; or
contacting the hydrocarbon reactant with a fixed bed of the supported transition metal catalyst, and irradiating while contacting.

9. The process of claim 1, wherein:
hydrolyzing is conducted at a temperature from 0° C. to 100° C.; and
hydrolyzing comprises contacting the reduced transition metal catalyst with a hydrolysis agent comprising water, steam, an alcohol agent, an acid agent, an alkaline agent, or any combination thereof.

10. The process of claim 1, further comprising a step of separating at least a portion of the alcohol compound and/or the carbonyl compound from the reaction product after step (ii).

11. The process of claim 1, further comprising a step of separating at least a portion of the hydrocarbon reactant from the reaction product after step (ii), and wherein the at least a portion of the hydrocarbon reactant is recycled and irradiated with the supported transition metal catalyst again.

12. The process of claim 1, further comprising:
separating at least a portion of the reduced transition metal catalyst from the reaction product after step (ii); and
calcining the at least a portion of the reduced transition metal catalyst to regenerate the supported transition metal catalyst.

13. The process of claim 1, wherein:
a conversion of the hydrocarbon reactant is at least 10 wt. %; and/or
a molar yield of the alcohol compound and/or the carbonyl compound is from 0.01 to 5 moles of the alcohol compound and/or the carbonyl compound per mole of transition metal in the supported transition metal catalyst.

14. The process of claim 1, wherein the supported transition metal catalyst comprises vanadium.

15. A process for converting a hydrocarbon reactant into an alcohol compound and/or a carbonyl compound, the process comprising:
(I) irradiating the hydrocarbon reactant and a supported transition metal catalyst comprising molybdenum, tungsten, vanadium, or a combination thereof, with a light beam at a wavelength in the UV-visible spectrum to reduce at least a portion of the supported transition metal catalyst to form a reduced transition metal catalyst;
(II) subjecting the reduced transition metal catalyst to an oxidizing atmosphere; and
(III) hydrolyzing the reduced transition metal catalyst to form a reaction product comprising the alcohol compound and/or the carbonyl compound.

16. The process of claim 15, wherein;
the light beam is from a blue light source or a UV light source;
the light beam comprises wavelengths above 350 nm and below 500 nm;
the hydrocarbon reactant and the supported transition metal catalyst are irradiated with an illuminance of at least 5000 lux; or
any combination thereof.

17. The process of claim 15, wherein:
- a conversion of the hydrocarbon reactant is at least 10 wt. %; and/or
- a molar yield of the alcohol compound and/or the carbonyl compound is from 0.01 to 5 moles of the alcohol compound and/or the carbonyl compound per mole of transition metal in the supported transition metal catalyst.

\* \* \* \* \*